(12) United States Patent
Karube et al.

(10) Patent No.: US 7,303,867 B2
(45) Date of Patent: Dec. 4, 2007

(54) METHOD FOR DETECTING TARGET NUCLEOTIDE SEQUENCES

(75) Inventors: Isao Karube, Yokohama (JP); Teru Kato, Yokohama (JP)

(73) Assignee: Katayanagi Institute (JP)

( * ) Notice: Subject to any disclaimer, the term of this patent is extended or adjusted under 35 U.S.C. 154(b) by 359 days.

(21) Appl. No.: 10/149,869

(22) PCT Filed: Dec. 15, 2000

(86) PCT No.: PCT/JP00/08909

§ 371 (c)(1),
(2), (4) Date: Dec. 23, 2002

(87) PCT Pub. No.: WO01/44509

PCT Pub. Date: Jun. 21, 2001

(65) Prior Publication Data

US 2003/0170650 A1    Sep. 11, 2003

(30) Foreign Application Priority Data

Dec. 16, 1999   (JP)   ............................. 11-357913

(51) Int. Cl.
*C12Q 1/68* (2006.01)
*C07H 21/04* (2006.01)

(52) U.S. Cl. .......................... 435/6; 536/23.1
(58) Field of Classification Search ............... None
See application file for complete search history.

(56) References Cited

U.S. PATENT DOCUMENTS 5,633,133 A   5/1997   Long et al. ................ 435/6

FOREIGN PATENT DOCUMENTS

WO    WO 01/23612 A2   4/2001
WO    WO 01/23612 A3   4/2001

OTHER PUBLICATIONS

Porta et al. (1995) Biotechnology 13:161-164.*
Guo et al. (1990) Biochemistry 29:3407-3412.*
Prudent et al. (1994) Science 264:1924-1927.*
Kato et al., 2005, Nucleic Acids Res. 49:359-360.*
Stojanovic et al. (2000) J. Am. Chem. Soc. 122:11547-11548.*
Laatikainen et al. (1977) Obstet. Gynecol. 50:313-318.*
Bier et al. "Nucleic acid based sensors." *EXS*. 1997;80:97-120.
Broude "Stem-loop oligonucleotides: a robust tool for molecular biology and biotechnology." *Trends Biotechnol.* Jun. 2002;20(6):249-56.
Cairns et al. "Nucleic acid mutation analysis using catalytic DNA." *Nucleic Acids Res.* Feb. 1, 2000;28(3):e9,i-vi.
Fukusaki et al. "DNA aptamers that bind to chitin." *Bioorg. Med. Chem. Lett.* Mar. 6, 2000;10(5):423-5.
Guo et al. "Site-specific interaction of intercalating drugs with a branched DNA molecule." *Biochemistry.* Mar. 21, 1989;28(6):2355-9.
Hale et al. "DNA aptamer targets translational editing motif in a tRNA synthetase." *Tetrahedron* 1997;53(35):11985-11994.
Holeman et al. "Isolation and characterization of fluorophore-binding RNA aptamers." *Fold. Des.* 1998;3(6):423-31.
Huizenga et al. "A DNA aptamer that binds adenosine and ATP." *Biochemistry.* Jan. 17, 1995;34(2):656-65.
James "The potential application of ribozymes for the treatment of hematological disorders." *J. Leukoc. Biol.* Sep. 1999;66(3):361-8.
Jhaveri et al. "In vitro selection of phosphorothiolated aptamers." *Bioorg. Med. Chem. Lett.* Sep. 8, 1998;8(17):2285-90.
Lu et al. "Drug binding by branched DNA: selective interaction of the dye stains—all with an immobile junction." *Biochemistry.* Apr. 3, 1990;29(13):3407-12.
Porta, et al. "An allosteric hammerhead ribozyme." *Biotechnology (N Y).* Feb. 1995;13(2):161-4.
Sassanfar et al. "An RNA motif that binds ATP." *Nature.* Aug. 5, 1993;364(6437):550-3.
Stühmeier et al. "Global structure of three-way DNA junctions with an without additional unpaired bases: a fluorescence resonance energy transfer analysis." *Biochemistry.* Nov. 4, 1997;36(44):13530-8.
Wilson et al. "Functional requirements for specific ligand recognition by a biotin-binding RNA pseudoknot." *Biochemistry.* Oct. 13, 1998;37(41):14410-9.
Bock, L.C. et al. "Selection of single-stranded DNA molecules that bind and inhibit human thrombin" *Nature* 355(6360):564-6 (Feb. 6, 1992).
Ellington, A.D. et al. "In vitro selection of RNA molecules that bind specific ligands" *Nature* 346(6287):818-22 (Aug. 30, 1990).
Jackson, B.A. et al. "Recognition of DNA base mismatches by a rhodium intercalator" *J. Am. Chem. Soc.* 119:12986-7 (1997).
Kato, T. et al. "In vitro selection of DNA aptamers which bind to cholic acid" *Biochimica et Biophysica Acta* 1493(1-2):12-18 (2000).
Kato, T. et al. "Interaction of three-way DNA junctions with steroids" *Nucleic Acids Research* 28(9):1963-1968 (2000).
Lu, M. et al. "Effect of sequence on the structure of three-arm DNA junctions" *Biochemistry* 30(24):5815-20 (Jun. 18, 1991).
Tuerk, C. et al. "Systematic evolution of ligands by exponential enrichment: RNA ligands to bacteriophage T4 DNA polymerase" *Science* 249(4968):505-10 (Aug. 1990).
Wu, L. et al. "An allosteric synthetic DNA" *Nucleic Acids Research* 27(6):1512-16 (1999).

* cited by examiner

*Primary Examiner*—Sean McGarry
*Assistant Examiner*—Louis Wollenberger
(74) *Attorney, Agent, or Firm*—Jeanne M. DiGiorgio, Esq.; Lahive & Cockfield, LLP.

(57) ABSTRACT

A method for detecting nucleic acids wherein the binding activity of a nucleic acid aptamer, which is formed by the hybridization of a target nucleotide sequence and a probe, is detected using the binding with a ligand as an index has been provided. Utilizing a structure such as the three-way junction, whose binding activity significantly changes depending on a mismatch of a single nucleotide, as the nucleic acid aptamer SNP can be detected.

4 Claims, 21 Drawing Sheets

Figure 2
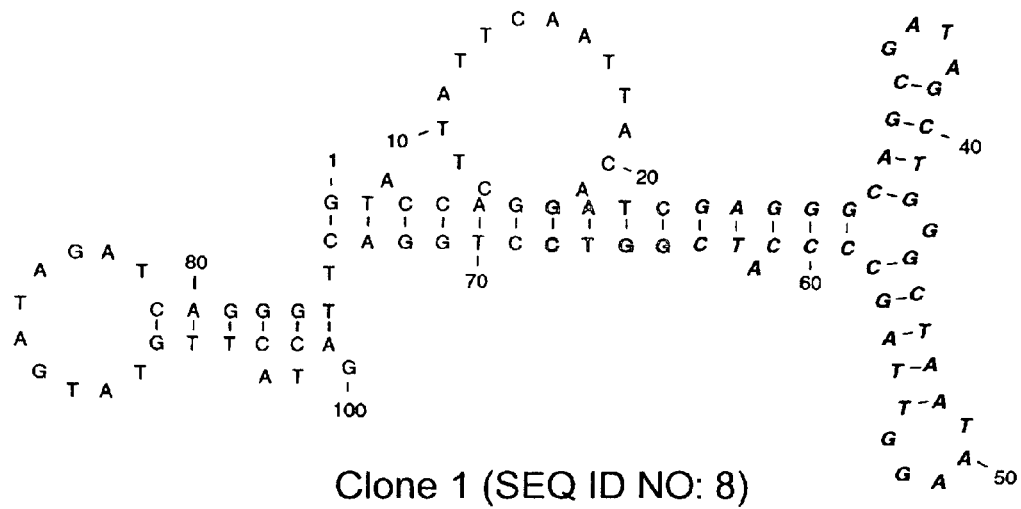
Clone 1 (SEQ ID NO: 8)
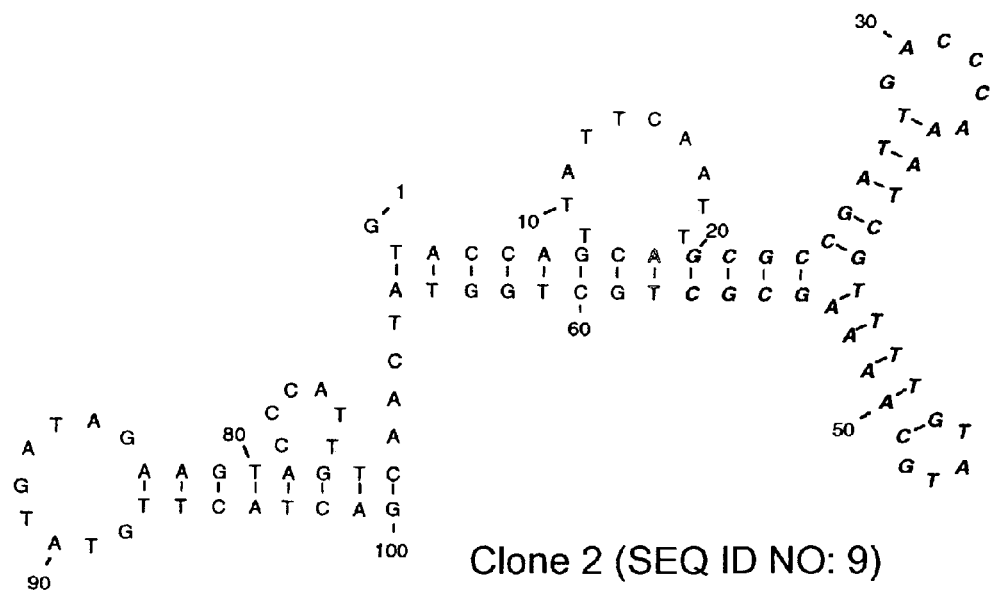
Clone 2 (SEQ ID NO: 9)

Figure 4
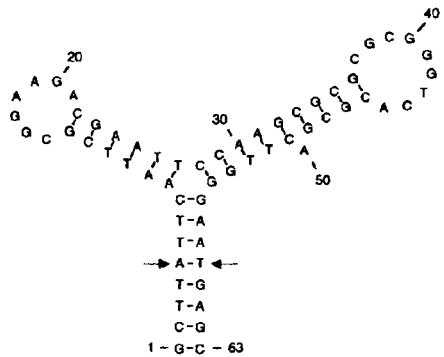
Clone 5 (SEQ ID NO: 10)
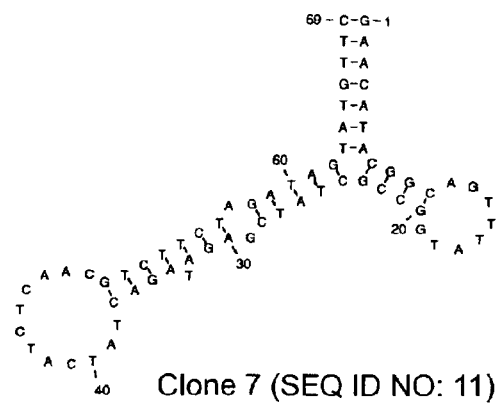
Clone 7 (SEQ ID NO: 11)
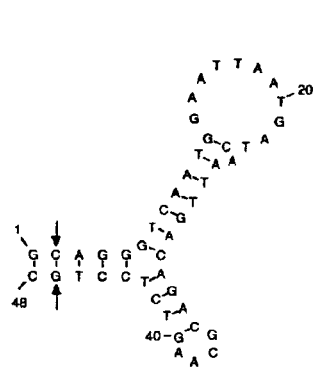
Clone 9 (SEQ ID NO: 12)
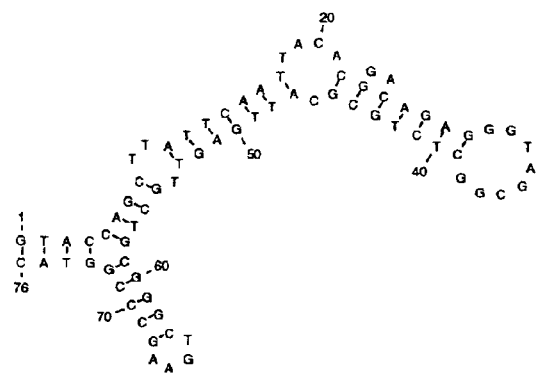
Clone 11 (SEQ ID NO: 13)

Figure 5
Mutation analysis of ch2-40 (SEQ ID NO:7)
(a)
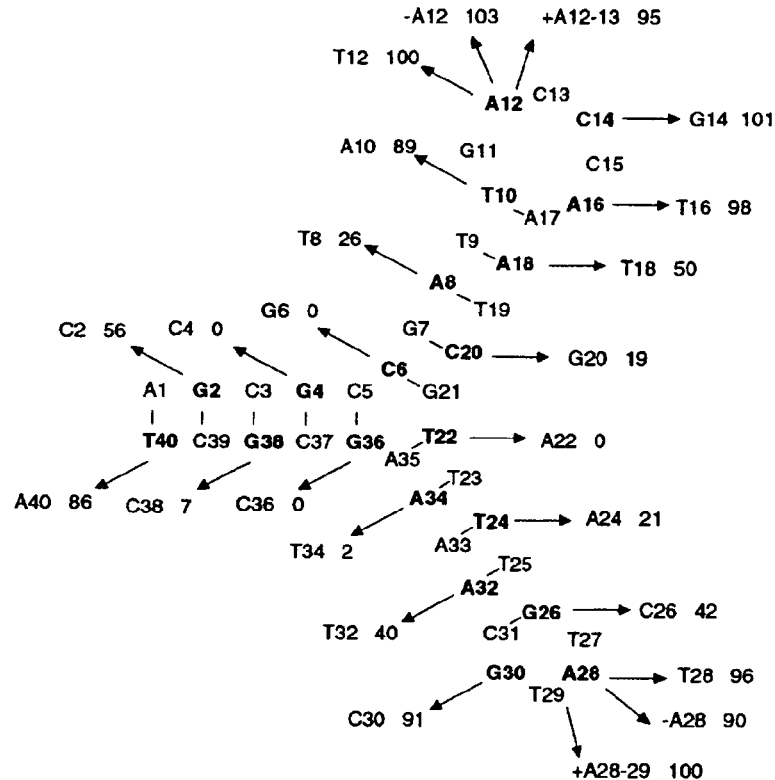
(b)
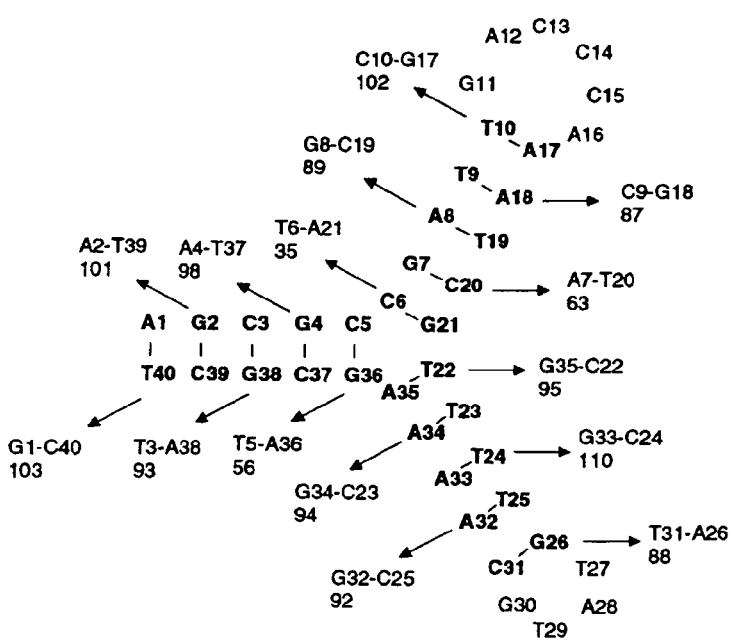

(SEQ ID NO: 38)

Figure 9

```c
#include<stdio.h>
#include<stdlib.h>
#include<string.h>
#include<ctype.h>
#include<time.h>
include<stdarg.h> define LINE_SIZE 256
define DEFAULT_CONTROL "control.txt"

#define REG_MAX 512
#define MAX_FILE 40
define MAX_CASE 15 counts char BASE[4]={'A', 'C', 'G', 'T'};

int debug = 1;
int version = 0;
char *log_file = "log.txt";
int method = 0;
int seq_file_num = 0;
int str_file_num = 0;
char *sequence_file[MAX_FILE];
char *structure_file[MAX_FILE];
int random_length = 0;
int random_number = 0;
unsigned int random_seed = 0;
char *result_file = "result.txt";
int stem1_len_min = 3;
int stem2_len_min = 3;
int stem3_len_min = 3;
int loop2_len_min = 4;
int loop3_len_min = 4;
int loop2_len_max = 1000;
int loop3_len_max = 1000;
int gap_max = 0;

FILE *log_fp=NULL;
char *seq;
int seq_len;
int stem1_cnt, stem1_str, stem1_end, stem1_len;
int stem2_cnt, stem2_str, stem2_end, stem2_len;
int stem3_cnt, stem3_str, stem3_end, stem3_len;
int reg_len = 0;

struct {
    int s1s, s1e, s1l, s2s, s2e, s2l, s3s, s3e, s3l;
} REG[REG_MAX];

int uprintf(const char *str, ...) {
    va_list arg_ptr;
    va_start(arg_ptr, str);
    vprintf(str, arg_ptr);
    if(log_fp!=NULL) vfprintf(log_fp, str, arg_ptr);
    va_end(arg_ptr);
    return(0);
}
```

Figure 10

```
int readFile(char *filename) {
  FILE *fp;
  char c;
  int i;
  if((fp = fopen(filename, "r")) == NULL) {
    uprintf("can't open %s\n", filename);
    exit(1);
  }
  seq_len = 0;
  while((c = getc(fp)) != EOF) {
    switch(c) {
    case '#':
      while(getc(fp) != '\n');
      break;
    case 'A':
    case 'C':
    case 'G':
    case 'U':
    case 'T':
    case 'a':
    case 'c':
    case 'g':
    case 'u':
    case 't':
      seq_len++;
      break;
    case ' ':
    case '\t':
    case '\n':
    case '\r':
      break;
    default:
      uprintf("Invalid character: '%c'\n", c);
      exit(1);
    }
  }
  fseek(fp, 0, SEEK_SET);
  if((seq=(char*)malloc(sizeof(char)*(seq_len+1)))==NULL) {
    uprintf("Not enough memory for seq\n");
    exit(1);
  }
  for(i=0; i<seq_len;) {
    switch(c = getc(fp)) {
    case '#':
      while(getc(fp) != '\n');
      break;
    case 'A':
    case 'C':
    case 'G':
    case 'T':
      seq[i++] = c;
      break;
    case 'U':
    case 'u':
      seq[i++] = 'T';
      break;
    case 'a':
    case 'c':
```

Figure 11

```
      case 'g':
      case 't':
        seq[i++] = toupper(c);
        break;
      case ' ':
      case '\t':
      case '\n':
      case '\r':
        break;
    }
  }
  seq[seq_len] = '\0';
  if(debug>=2) uprintf("sequence = %s\nseq_len = %d\n", seq,
seq_len);
  fclose(fp);
  return(0);
} char pair(char c) {
  switch(c) {
  case 'A':
    return('T');
  case 'T':
    return('A');
  case 'C':
    return('G');
  case 'G':
    return('C');
  }
  uprintf("pair: ivalid character 0x%02x '%c'", c, c);
  exit(1);
  return(0);
} int chkREG(int s1s, int s1e, int s1l, int s2s, int s2e, int s2l,
           int s3s, int s3e, int s3l) {
  int i;
  for(i=0; i<reg_len; i++) {
    if(s1s!=REG[i].s1s) continue;
    if(s1e!=REG[i].s1e) continue;
    if(s1l!=REG[i].s1l) continue;
    if(s2s!=REG[i].s2s) continue;
    if(s2e!=REG[i].s2e) continue;
    if(s2l!=REG[i].s2l) continue;
    if(s3s!=REG[i].s3s) continue;
    if(s3e!=REG[i].s3e) continue;
    if(s3l==REG[i].s3l) return(1);
  }
  return(0);
} int save(int s1s, int s1e, int s1l, int s2s, int s2e, int s2l,
         int s3s, int s3e, int s3l) {
  if(chkREG(s1s, s1e, s1l, s2s, s2e, s2l, s3s, s3e, s3l)==1)
return(0);
  if(reg_len>=REG_MAX) {
    uprintf("too many struct!: REG_MAX\n");
    exit(1);
  }
```

Figure 12

```
    REG[reg_len].s1s=s1s;
    REG[reg_len].s1e=s1e;
    REG[reg_len].s1l=s1l;
    REG[reg_len].s2s=s2s;
    REG[reg_len].s2e=s2e;
    REG[reg_len].s2l=s2l;
    REG[reg_len].s3s=s3s;
    REG[reg_len].s3e=s3e;
    REG[reg_len].s3l=s3l;
    reg_len++;
    return(1);
} int success2(int s1s, int s1e, int s1l, int s2s, int s2e, int s2l,
             int s3s, int s3e, int s3l) {
    int flag = 1;
    if(s1s+s1l<s2s && s1e-s1l>s3e && seq[s1s+s1l]==pair(seq[s1e-s1l])) {
        s1l++;
        success2(s1s, s1e, s1l, s2s, s2e, s2l, s3s, s3e, s3l);
        flag = 0;
    }
    if(s2s-1>=s1s+s1l && s2e+1<s3s && seq[s2s-1]==pair(seq[s2e+1])) {
        s2s--;
        s2e++;
        s2l++;
        success2(s1s, s1e, s1l, s2s, s2e, s2l, s3s, s3e, s3l);
        flag = 0;
    }
    if(s3s-1>s2e && s3e+1<=s1e-s1l && seq[s3s-1]==pair(seq[s3e+1])) {
        s3s--;
        s3e++;
        s3l++;
        success2(s1s, s1e, s1l, s2s, s2e, s2l, s3s, s3e, s3l);
        flag = 0;
    }
    if(flag == 1) {
        if(save(s1s, s1e, s1l, s2s, s2e, s2l, s3s, s3e, s3l)==1) {
            if(debug >= 3) uprintf("New struct found!\n");
        } else {
            if(debug >= 3) uprintf("Same struct.\n");
        };
    }
    return(0);
} int success(int s1s, int s1e, int s1l, int s2s, int s2e, int s2l,
            int s3s, int s3e, int s3l) {
    while(s1s>0 && s1e<seq_len-1) {
        if(seq[s1s-1]!=pair(seq[s1e+1])) break;
        s1s--;
        s1e++;
        s1l++;
    }
    while(s2s+s2l<s2e-s2l) {
        if(seq[s2s+s2l]!=pair(seq[s2e-s2l])) break;
        s2l++;
    }
```

Figure 13

```
   while(s3s+s3l<s3e-s3l) {
      if(seq[s3s+s3l]!=pair(seq[s3e-s3l])) break;
      s3l++;
   }
   success2(s1s, s1e, s1l, s2s, s2e, s2l, s3s, s3e, s3l);
   return(0);
} int chkStem3(void) {
      int c, i, j, k, flag;
      stem3_len = stem3_len_min;
      for(i=0; i<=gap_max; i++) {
            stem3_str = stem2_end+1+i;
            if(stem3_str>=seq_len) break;
            c = pair(seq[stem3_str]);
            for(j=stem1_end-stem1_len; j>stem1_end-stem1_len-
gap_max-1; j--) {
                  if(j-stem3_str+1<stem3_len_min*2+loop3_len_min ||
j-stem3_str+1>stem3_len_min*2+loop3_len_max) break;
                  if(seq[j]!=c) continue;
                  stem3_end = j;
                  for(flag=0, k=1; k<stem3_len_min; k++) {
                        if(seq[stem3_str+k]!=pair(seq[stem3_end-k]))
{
                              flag=1;
                              break;
                        }
                  }
                  if(flag==1) continue;
                  stem3_cnt++;
                  if(debug >= 3) {
                        uprintf("STEM3(5')%03d:", stem3_str+1);
                        for(k=0; k<stem3_len; k++) uprintf("%c",
seq[stem3_str+k]);
                        uprintf("\nSTEM3(3')%03d:", stem3_end+1);
                        for(k=0; k<stem3_len; k++) uprintf("%c",
seq[stem3_end-k]);
                        uprintf("\n");
                  }
                  success(stem1_str, stem1_end, stem1_len,
stem2_str, stem2_end,
                        stem2_len, stem3_str, stem3_end, stem3_len);
            }
      }
      return(0);
} int chkStem2(void) {
      int c, i, j, k, flag;
      stem2_len = stem2_len_min;
      for(i=0; i<=gap_max; i++) {
            stem2_str = stem1_str+stem1_len+i;
            if(stem2_str>=seq_len) break;
            c = pair(seq[stem2_str]);
            for(j=__min(stem1_end-stem1_len,
stem2_str+stem2_len_min*2+loop2_len_max-1);
j>stem2_str+stem2_len_min*2+loop2_len_min-2; j--) {
                  if(seq[j]!=c) continue;
                  stem2_end = j;
```

Figure 14

```
                        for(flag=0, k=1; k<stem2_len_min; k++) {
                                if(seq[stem2_str+k]!=pair(seq[stem2_end-k]))
{
                                        flag=1;
                                        break;
                                }
                        }
                        if(flag==1) continue;
                        stem2_cnt++;
                        if(debug >= 3) {
                                uprintf("STEM2(5')%03d:", stem2_str+1);
                                for(k=0; k<stem2_len; k++) uprintf("%c",
seq[stem2_str+k]);
                                uprintf("¥nSTEM2(3')%03d:", stem2_end+1);
                                for(k=0; k<stem2_len; k++) uprintf("%c",
seq[stem2_end-k]);
                                uprintf("¥n");
                        }
                        chkStem3();
                }
        }
        return(0);
} int chkDNA(void) {
        int c, i, j, k, flag;
        reg_len = 0;
        stem1_cnt = 0;
        stem2_cnt = 0;
        stem3_cnt = 0;
        stem1_len = stem1_len_min;
        for(i=0; i<seq_len-stem1_len_min*2+1; i++) {
                stem1_str = i;
                c = pair(seq[stem1_str]);
                for(j=seq_len-1; j>stem1_str+stem1_len_min*2-2; j--) {
                        if(seq[j]!=c) continue;
                        stem1_end = j;
                        for(flag=0, k=1; k<stem1_len_min; k++) {
                                if(seq[stem1_str+k]!=pair(seq[stem1_end-k]))
{
                                        flag=1;
                                        break;
                                }
                        }
                        if(flag==1) continue;
                        stem1_cnt++;
                        if(debug >= 3) {
                                uprintf("STEM1(5')%03d:", stem1_str+1);
                                for(k=0; k<stem1_len; k++) uprintf("%c",
seq[stem1_str+k]);
                                uprintf("¥nSTEM1(3')%03d:", stem1_end+1);
                                for(k=0; k<stem1_len; k++) uprintf("%c",
seq[stem1_end-k]);
                                uprintf("¥n");
                        }
                        chkStem2();
                }
        }
        if(debug>=2) {
```

Figure 15

```
                uprintf("stem1 count = %d¥n", stem1_cnt);
                uprintf("stem2 count = %d¥n", stem2_cnt);
                uprintf("stem3 count = %d¥n", stem3_cnt);
        }
        if(debug>=2) {
                uprintf("struct count = %d¥n", reg_len);
        }
        return(0);
} void writeFile(char *filename, char *subname) {
  FILE *fp;
  int s1s, s1e, s1l, s2s, s2e, s2l, s3s, s3e, s3l;
  int i, j, k;
  if((fp = fopen(filename, "w")) == NULL) {
    uprintf("can't open %s¥n", filename);
    exit(1);
  }
  fprintf(fp, "[DNA STRUCTURE REPORT]¥n");
  fprintf(fp, "SEQUENCE_FILE=%s¥n", subname);
  fprintf(fp, "STRUCTURE_FILE=%s¥n", filename);
  fprintf(fp, "SEQ_LENGTH=%d¥n", seq_len);
  fprintf(fp, "STEM1_LEN_MIN=%d¥n", stem1_len_min);
  fprintf(fp, "STEM2_LEN_MIN=%d¥n", stem2_len_min);
  fprintf(fp, "STEM3_LEN_MIN=%d¥n", stem3_len_min);
  fprintf(fp, "LOOP2_LEN_MIN=%d¥n", loop2_len_min);
  fprintf(fp, "LOOP3_LEN_MIN=%d¥n", loop3_len_min);
  fprintf(fp, "LOOP2_LEN_MAX=%d¥n", loop2_len_max);
  fprintf(fp, "LOOP3_LEN_MAX=%d¥n", loop3_len_max);
  fprintf(fp, "GAP_MAX=%d¥n", gap_max);
  fprintf(fp, "stem1 count: %d¥n", stem1_cnt);
  fprintf(fp, "stem2 count: %d¥n", stem2_cnt);
  fprintf(fp, "stem3 count: %d¥n", stem3_cnt);
  fprintf(fp, "struct count: %d¥n", reg_len);
  for(i=0; i<seq_len; i++) {
    if(i%30 == 0) fprintf(fp, "¥n%03d: ", i+1);
    else if(i%10 == 0) fprintf(fp, " ");
    fprintf(fp, "%c", seq[i]);
  }
  fprintf(fp, "¥n¥n");
  for(i=0; i<reg_len; i++) {
    s1s=REG[i].s1s;
    s1e=REG[i].s1e;
    s1l=REG[i].s1l;
    s2s=REG[i].s2s;
    s2e=REG[i].s2e;
    s2l=REG[i].s2l;
    s3s=REG[i].s3s;
    s3e=REG[i].s3e;
    s3l=REG[i].s3l;
    fprintf(fp, "struct[%d]¥n", i+1);
    if(s2e-s2s+1-s2l*2>0) {
       for(j=s2s-s1s+5-(s2e-s2s-s2l*2)/2; j>0; j--) fprintf(fp, " ");
       for(j=s2s+s2l; j<=s2e-s2l; j++) fprintf(fp, "%c", seq[j]);
       fprintf(fp, "¥n");
    }
    for(j=s2l-1; j>=0; j--) {
       for(k=(j==0||j==s2l-1)?s2s-s1s:s2s-s1s+4; k>0; k--)
```

Figure 16

```
fprintf(fp," ");
    if(j==0||j==s2l-1) fprintf(fp, "%03d:", s2s+j+1);
    fprintf(fp, "%c-%c", seq[s2s+j], seq[s2e-j]);
    if(j==0||j==s2l-1) fprintf(fp, ":%03d", s2e-j+1);
    fprintf(fp, "¥n");
}
if(s1s+s1l<s2s) {
    for(j=s1l+4; j>0; j--) fprintf(fp, " ");
    for(j=s1s+s1l; j<s2s; j++) fprintf(fp, "%c", seq[j]);
    fprintf(fp, "¥n");
}
fprintf(fp, "%03d:", s1s+1);
for(j=0; j<s1l; j++) fprintf(fp, "%c", seq[s1s+j]);
fprintf(fp, ":%03d¥n   ",s1s+s1l);
for(j=0; j<s1l; j++) fprintf(fp, "|", seq[s1s+j]);
if(s3s-s2e>1) {
    for(j=s2s-s1s-s1l+3; j>0; j--) fprintf(fp, " ");
    for(j=s2e+1; j<s3s; j++) fprintf(fp, "%c", seq[j]);
}
fprintf(fp, "¥n");
fprintf(fp, "%03d:", s1e+1);
for(j=0; j<s1l; j++) fprintf(fp, "%c", seq[s1e-j]);
fprintf(fp, ":%03d¥n", s1e-s1l+2);
if(s3e<s1e-s1l) {
    for(j=s1l+4; j>0; j--) fprintf(fp, " ");
    for(j=s1e-s1l; j>s3e; j--) fprintf(fp, "%c", seq[j]);
    fprintf(fp, "¥n");
}
for(j=0; j<s3l; j++) {
    for(k=(j==0||j==s3l-1)?s1e-s3e:s1e-s3e+4; k>0; k--)
fprintf(fp, " ");
    if(j==0||j==s3l-1) fprintf(fp, "%03d:", s3e-j+1);
    fprintf(fp, "%c-%c", seq[s3e-j], seq[s3s+j]);
    if(j==0||j==s3l-1) fprintf(fp, ":%03d", s3s+j+1);
    fprintf(fp, "¥n");
}
if(s3e-s3s+1-s3l*2>0) {
    for(j=s1e-s3e+5-(s3e-s3s-s3l*2)/2; j>0; j--) fprintf(fp, "
");
    for(j=s3e-s3l; j>=s3s+s3l; j--) fprintf(fp, "%c", seq[j]);
    fprintf(fp, "¥n");
}
    fprintf(fp, "¥n");
}
} int FileMethod(void) {
    int i;
    if(seq_file_num!=str_file_num) {
        uprintf("SEQUENCE_FILE & STRUCTURE_FILE must be same number!");
        exit(1);
    }
    for(i=0; i<seq_file_num; i++) {
        uprintf("'%s'->'%s': ", sequence_file[i], structure_file[i]);
        readFile(sequence_file[i]);
        chkDNA();
        writeFile(structure_file[i], sequence_file[i]);
```

Figure 17

```
                uprintf("%d structure(s)¥n", reg_len);
        }
        return(0);
} int RandomMethod(void) {
        int i, j, p=10;
        FILE *fp;
        int case_num[MAX_CASE];
        if(random_seed==0) random_seed = (unsigned) time(NULL);
        for(i = 0; i<MAX_CASE; i++) case_num[i] = 0;
        uprintf("RESULT_FILE=%s¥n", result_file);
        if((fp=fopen(result_file, "wt"))==NULL) {
                uprintf("can't open '%s'!¥n", result_file);
                exit(1);
        }
        fprintf(fp, "[RANDOM METHOD REPORT]¥n");
        fprintf(fp, "RANDOM_LENGTH=%d¥n", random_length);
        fprintf(fp, "RANDOM_NUMBER=%d¥n", random_number);
        fprintf(fp, "RANDOM_SEED=%d¥n", random_seed);
        fprintf(fp, "STEM1_LEN_MIN=%d¥n", stem1_len_min);
        fprintf(fp, "STEM2_LEN_MIN=%d¥n", stem2_len_min);
        fprintf(fp, "STEM3_LEN_MIN=%d¥n", stem3_len_min);
        fprintf(fp, "LOOP2_LEN_MIN=%d¥n", loop2_len_min);
        fprintf(fp, "LOOP3_LEN_MIN=%d¥n", loop3_len_min);
        fprintf(fp, "LOOP2_LEN_MAX=%d¥n", loop2_len_max);
        fprintf(fp, "LOOP3_LEN_MAX=%d¥n", loop3_len_max);
        fprintf(fp, "GAP_MAX=%d¥n", gap_max);
        srand(random_seed);
        seq_len = random_length;
        if((seq=(char*)malloc(sizeof(char)*(seq_len+1)))==NULL) {
                uprintf("Not enough memory for sequence¥n");
                exit(1);
        }
        uprintf("Now started.¥n");
        for(i = 0; i < random_number; i++) {
                if(i*100>p*random_number) {
                        uprintf("%d%% was done.¥n", p);
                        p+=10;
                }
                for(j = 0; j < seq_len; j++) seq[j] = BASE[rand()&3];
                seq[seq_len] = 0;
                chkDNA();
                if(reg_len < MAX_CASE-1) case_num[reg_len]++; else
case_num[MAX_CASE-1]++;
        }
        uprintf("Now completed.¥n");
        fprintf(fp, "no structure: %d(%.1f%%)¥n", case_num[0],
((float) case_num[0])*100/random_number);
        for(i = 1; i < MAX_CASE-1; i++) {
                fprintf(fp, "%d structure(s): %d(%.1f%%)¥n", i,
case_num[i], ((float) case_num[i])*100/random_number);
        }
        fprintf(fp, "over %d structure(s): %d(%.1f%%)¥n", i,
case_num[i], ((float) case_num[i])*100/random_number);
        fclose(fp);
        return(0);
}
```

Figure 18

```
int line2word(const char *str, char *key, char *value) {
    int i=0, j=0, k=0;
    do {
        if(str[i] == 0 || str[i] == '¥n') return(0);
        if(str[i] != ' ' && str[i] != '¥t') break;
        i++;
    } while(1);
    if(str[i] == '#') return(0);
    while(__iscsym(str[i])) key[j++] = str[i++];
    key[j] = 0;
    value[k] = 0;
    do {
        if(str[i] == 0 || str[i] == '¥n') return(1);
        if(str[i] != ' ' && str[i] != '¥t') break;
        i++;
    } while(1);
    if(str[i++] != '=') {
        uprintf("%s don't have '='!¥n", key);
        exit(1);
    }
    do {
        if(str[i] == 0 || str[i] == '¥n') return(1);
        if(str[i] != ' ' && str[i] != '¥t') break;
        i++;
    } while(1);
    while(str[i] != 0 && str[i] != '¥n' && str[i] != ' ' && str[i] != '¥t') value[k++] = str[i++];
    value[k] = 0;
    do {
        if(str[i] == 0 || str[i] == '¥n') return(1);
        if(str[i] != ' ' && str[i] != '¥t') break;
        i++;
    } while(1);
    uprintf("'%s=%s' has extra charctors!¥n", key, value);
    exit(1);
    return(-1);
} int load_control(const char *control_file) {
    FILE *fp;
    char str[LINE_SIZE], key[LINE_SIZE], value[LINE_SIZE];
    if((fp = fopen(control_file, "rt")) == NULL) {
        uprintf("can't open!¥n");
        exit(1);
    }
    while(fgets(str, LINE_SIZE, fp)) {
        if(line2word(str, key, value)==0) continue;
        if(stricmp(key, "VERSION") == 0) {
            version = atoi(value);
            continue;
        }
        if(stricmp(key, "DEBUG") == 0) {
            debug = atoi(value);
            continue;
        }
        if(stricmp(key, "LOG_FILE") == 0) {
            log_file = strdup(value);
            continue;
        }
```

Figure 19

```
              if(stricmp(key, "METHOD") == 0) {
                  if(stricmp(value, "FILE") == 0) method = 1;
                  else if(stricmp(value, "RANDOM") == 0) method = 2;
                  else {
                      uprintf("METHOD has illegal word:'%s'¥n",
value);
                      exit(1);
                  }
                  continue;
              }
              if(stricmp(key, "SEQUENCE_FILE") == 0) {
                  if(seq_file_num>=MAX_FILE) {
                      uprintf("too many SEQUENCE_FILE!¥n");
                      exit(1);
                  }
                  sequence_file[seq_file_num++] = strdup(value);
                  continue;
              }
              if(stricmp(key, "STRUCTURE_FILE") == 0) {
                  if(str_file_num>=MAX_FILE) {
                      uprintf("too many STRUCTURE_FILE!¥n");
                      exit(1);
                  }
                  structure_file[str_file_num++] = strdup(value);
                  continue;
              }
              if(stricmp(key, "RANDOM_LENGTH") == 0) {
                  random_length = atoi(value);
                  continue;
              }
              if(stricmp(key, "RANDOM_NUMBER") == 0) {
                  random_number = atoi(value);
                  continue;
              }
              if(stricmp(key, "RANDOM_SEED") == 0) {
                  random_seed = atoi(value);
                  continue;
              }
              if(stricmp(key, "RESULT_FILE") == 0) {
                  result_file = strdup(value);
                  continue;
              }
              if(stricmp(key, "STEM1_LEN_MIN") == 0) {
                  stem1_len_min = atoi(value);
                  continue;
              }
              if(stricmp(key, "STEM2_LEN_MIN") == 0) {
                  stem2_len_min = atoi(value);
                  continue;
              }
              if(stricmp(key, "STEM3_LEN_MIN") == 0) {
                  stem3_len_min = atoi(value);
                  continue;
              }
              if(stricmp(key, "LOOP2_LEN_MIN") == 0) {
                  loop2_len_min = atoi(value);
                  continue;
              }
              if(stricmp(key, "LOOP3_LEN_MIN") == 0) {
```

Figure 20

```
                loop3_len_min = atoi(value);
                continue;
        }
        if(stricmp(key, "LOOP2_LEN_MAX") == 0) {
                loop2_len_max = atoi(value);
                continue;
        }
        if(stricmp(key, "LOOP3_LEN_MAX") == 0) {
                loop3_len_max = atoi(value);
                continue;
        }
        if(stricmp(key, "GAP_MAX") == 0) {
                gap_max = atoi(value);
                continue;
        }
        uprintf("Keyword '%s' is unknown!¥n", key);
        exit(1);
    }
    return(0);
} void exit_procedure(void) {
    uprintf("Please enter to exit.:");
    if(log_fp!=NULL) fclose(log_fp);
    getchar();
} int main(int argc, char *argv[]) {
    atexit(exit_procedure);
    char *control_file = argc < 2 ? DEFAULT_CONTROL : argv[0];
    load_control(control_file);
    log_fp = fopen(log_file, "wt");
    uprintf("DNAstructure (C)1988-2000 TARO¥n");
    uprintf("CONTROL_FILE=%s¥n", control_file);
    uprintf("LOG_FILE=%s¥n", log_file);
    uprintf("METHOD=%s¥n", method == 1 ? "FILE" : method == 2 ?
"RANDOM" : "(none)");
    if(debug) {
        int i;
        uprintf("VERSION=%d¥n", version);
        uprintf("DEBUG=%d¥n", debug);
        for(i=0; i<seq_file_num; i++)
uprintf("SEQUENCE_FILE[%d]=%s¥n", i, sequence_file[i]);
        for(i=0; i<str_file_num; i++)
uprintf("STRUCTURE_FILE[%d]=%s¥n", i, structure_file[i]);
        uprintf("RANDOM_LENGTH=%d¥n", random_length);
        uprintf("RANDOM_NUMBER=%d¥n", random_number);
        uprintf("RANDOM_SEED=%d¥n", random_seed);
        uprintf("RESULT_FILE=%d¥n", result_file);
        uprintf("STEM1_LEN_MIN=%d¥n", stem1_len_min);
        uprintf("STEM2_LEN_MIN=%d¥n", stem2_len_min);
        uprintf("STEM3_LEN_MIN=%d¥n", stem3_len_min);
        uprintf("LOOP2_LEN_MIN=%d¥n", loop2_len_min);
        uprintf("LOOP3_LEN_MIN=%d¥n", loop3_len_min);
        uprintf("LOOP2_LEN_MAX=%d¥n", loop2_len_max);
        uprintf("LOOP3_LEN_MAX=%d¥n", loop3_len_max);
        uprintf("GAP_MAX=%d¥n", gap_max);
    }
    if(method==1) {
```

Figure 21

```
            FileMethod();
    } else if(method==2) {
            RandomMethod();
    } else {
            uprintf("no method!\n");
            exit(1);
    }
    return(0);
}
```

METHOD FOR DETECTING TARGET NUCLEOTIDE SEQUENCES

This Application is a 35 USC 371(c) National Stage Application of PCT/JP00/08909, filed Dec. 15, 2000.

This application claims the benefit of prior-filed Japanese patent application 11/357913 (filed Dec. 16, 1999) entitled "Method of Detecting Target Base Sequence". The entire content of the above-referenced application is incorporated herein by reference.

A compact disc containing the source code listing of the software program used for selecting nucleotide sequences forming nucleic acid aptamers of the present invention entitled "Computer Program Listing Appendix" (20.5 KB, created on Jul. 31, 2006) has been filed with the U.S. Patent and Trademark Office, the entire contents of which is herein incorporated by reference.

TECHNICAL FIELD

The present invention relates to a method for detecting specific nucleotide sequences (hereinafter referred to as "target nucleotide sequences") in a sample.

BACKGROUND ART

Methods analyzing nucleotide sequences based on their complementarity enable direct analysis of genetic features. Thus, such methods are highly useful for diagnosing genetic diseases, canceration, microorganisms, etc. In addition, methods for amplifying nucleotide sequences, such as PCR, may be applied as such methods enable detection with high sensitivity without any procedures, unlike cell culturing that requires a lot of time and trouble.

Various methods are reported for detecting hybridization of complementary nucleotide sequences. The most fundamental reaction principle widely used is the Southern blot analysis, wherein a sample DNA is immobilized on a nitrocellulose filter to be reacted with a labeled probe. When the sample DNA contains a nucleotide sequence complementary to the probe, the labeled probe is trapped on the nitrocellulose filter through hybridization. A probe for trapping sample DNAs can be used to save the trouble of immobilizing the sample DNAs. In such cases, the labeled probe is trapped in the following order: [solid phase]-[trap probe]-[sample DNA]-[labeled probe]. Regardless of the type of method to be used, a common problem is the adsorption of labeled probes to solid phase independent of the target nucleotide sequence. The non-specific adsorption of labeled probes is the major factor for decreased detection sensitivity. Thus, hybridizations are typically performed in a reaction solution comprising a large quantity of carriers with unrelated nucleotide sequences. Further, the influence of non-specific adsorption is suppressed by thoroughly conducting post-hybridization washing. However, these measures are not sufficient.

Furthermore, methods for analyzing nucleic acids, which do not require the separation of unhybridized labeled probes from the target, are known in the art. For example, a method for detecting homogeneity based upon the difference in the signal of fluorescent label, which changes due to the state of the chains (i.e., single- or double-stranded nucleic acids), is of practical use. The sensitivity of the method is affected by the background signal. Therefore, the problem of the method is that high sensitivity is difficult to achieve with this method. Thus, the method is typically used only when the DNA to be analyzed has been pre-amplified by methods such as PCR.

On the other hand, with the progress of the Human Genome Project, attention has been paid to single nucleotide polymorphism (hereinafter abbreviated as SNP) due to the possibility that the difference of the therapeutic effect of a drug including side effects, and the presence or absence of predisposition to various diseases may be explained by SNP. For example, once a serious side effect of a drug is affected by genetic predisposition based upon SNP, accidents due to the administration of the drug can be avoided by analyzing patients for the presence of SNP associated with the side effect. The term "SNP" refers to a single nucleotide polymorphism in nucleotide sequences of the genome. The human genome, which comprises 3 billion nucleotides, has been suggested to contain approximately one SNP every 1000 nucleotides. The term "SNP" literally refers to a single-nucleotide difference in the genome. As a mater of fact, highly advanced technologies are required to precisely detect single-nucleotide differences. Two nucleic acids having nucleotide sequences complementary to each other hybridize even when the two sequences are not perfectly complementary to each other. Therefore, direct detection of single nucleotide differences by the hybridization method as described above has been found to be difficult.

Currently, the method for detecting known SNPs includes the PCR-SSCP method. This method requires isolation by electrophoresis and thus is not suitable for treating subjects on a large-scale. Hence, a new SNP-detection method without such a drawback is required in the art.

A phenomenon wherein a nucleic acid with specific structure specifically binds to proteins and such based on a different principle from that of hydrogen-bond formation between complementary nucleotide sequences has also been known in the art. Such affinity of the nucleic acid is utilized in the SELEX method (systematic evolution of ligands by exponential enrichment) for selecting nucleic acid molecules with higher affinity in vitro (Nature 355, 564-566, 1990). A nucleic acid with a high binding affinity for a ligand can be obtained by the SELEX method through a repetitive reaction that comprises the steps of contacting the ligand with a library of RNAs having random nucleotide sequences, then recovering the RNAs bound to the ligand, amplifying the recovered RNAs by RT-PCR, transcribing RNAs using the amplified and purified products as templates, and contacting the transcribed RNAs to the ligand. However, it is not generally known that such nucleic acid molecules with selected affinity can be used in various hybridization assays. Particularly, no report exists that indicates the possibility that such nucleic acid molecules are applicable in the detection of SNPs, wherein discrimination of a single nucleotide is required.

DISCLOSURE OF THE INVENTION

The object of the present invention is to provide a principle, which is based on a novel concept, for detecting a target nucleotide sequence comprising a specific sequence. More specifically, the object of the present invention is to utilize the binding affinity of nucleic acids in a method for detecting target nucleotide sequences; the binding was discovered by the present inventors and it was found that the binding is based on a different principle as that of hybridization between complementary nucleotide sequences. Another object of the present invention is to provide a method for detecting SNPs based on this novel principle. Another object of the present invention is to provide nucleic acids having a novel structure responsible for ligand-binding activity, thereby being useful for detecting nucleic acids.

The present inventors conceived that the structure of a nucleic acid, such as DNA, and various biochemical activities of such nucleic acids might be utilized as a novel means to establish a method for detecting nucleic acids in a nucleotide sequence-specific manner. Then, they confirmed that the binding affinity of a nucleic acid toward low-molecular-weight compounds depends on the nucleotide sequence of the nucleic acid constituting a specific structure, for example, the binding affinity greatly varied by substitutions of only a single nucleotide. Based on this finding, the present inventors discovered that a more specific method for detecting nucleotide sequences can be established by applying the ligand-binding affinity of nucleic acids to hybridization assays. Further, the present inventors also discovered that SNPs could be detected by the method for detecting nucleic acids based on the binding activity to a ligand; and completed the present invention. Specifically, the present invention relates to a method for detecting nucleic acids, the application of this method to the detection of SNPs, and nucleic acids with a novel structure enabling the detection methods as follows:

[1] a method for detecting a target nucleotide sequence, which comprises the steps:
 (a) hybridizing a probe to the target nucleotide sequence to form a nucleic acid aptamer having the binding affinity for a ligand; and
 (b) detecting the presence of the target nucleotide sequence using the affinity of the aptamer as an index;

[2] the method of [1], wherein the target nucleotide sequence contains a single nucleotide polymorphism and the affinity of the probe for the ligand vary depending on the substitution of the single nucleotide in the target nucleotide sequence;

[3] a probe that acquires the binding affinity for a ligand by the hybridization with the target nucleotide sequence;

[4] the probe of [3], which forms a structure wherein three or more stems intersect one another by the hybridization with the target nucleotide sequence, and binds to the ligand at the region where the stems intersect;

[5] the probe of [4], which comprises three stems wherein at least two of the three base pairs constituting the junction are G-C nucleotide pairs;

[6] the probe of [4], wherein each stem is longer than three base pairs;

[7] a nucleic acid aptamer, which has three or more stems and binds with the ligand at the position where the stems intersect; and

[8] a reagent for detecting target nucleotide sequences, which comprises the probe of [4].

Furthermore, the present invention also relates to the use of an oligonucleotide, in the detection of a target nucleotide sequence, wherein the oligonucleotide can form a nucleic acid aptamer having the binding affinity for a ligand through hybridization with the target nucleotide sequence.

Further, the present invention relates to a method for selecting a nucleotide sequence constituting an oligonucleotide that hybridizes with a target nucleotide sequence to form a nucleic acid aptamer, which has the binding affinity for a ligand, and a computer program to perform the method. According to the method for selecting a nucleotide sequence of the present invention, first, complementary nucleotide sequences between a target nucleotide sequence and an oligonucleotide are detected to assess whether they can form a first stem. The method further comprises the step of assessing, when it is concluded that the first stem can be formed, whether a second and a third stem can be formed with the nucleotide sequence of the region excluding the nucleotide sequence required for the formation of the first stem. On the other hand, the computer program of the present invention comprises algorithm to perform these steps.

Herein, the phrase "nucleic acid aptamer" refers to a nucleic acid having the binding activity for a ligand. The term "nucleic acid aptamer" refers to a nucleic acid molecule having at least a pair of intramolecular or intermolecular complementary nucleotide sequences and affinity for a ligand due to the hybridization of the complementary nucleotide sequences. A representative nucleic acid aptamer of the present invention consists of double-stranded portion (hybrid) formed by the hybridization of the above-mentioned complementary nucleotide sequences, and single-stranded portion, which doesn't form a hybrid. The nucleic acid aptamer of the present invention generally forms a conformation specific for each aptamer in the above-mentioned single-stranded portion through hydrogen bonding, base stacking, or hydrophobic interaction. Interactions particularly important for the formation of conformation are hydrogen bond and base stacking. Moreover, particularly important types of hydrogen bonds include base pairing, such as Watson-Crick type, non-Watson-Crick type, and G-quartet.

The binding affinity of a nucleic acid aptamer for a ligand depends on its conformation. Thus, for example, under conditions where it is hard to maintain the nucleic acid hybrid, the aptamer does not form the conformation, losing its binding affinity. The conformation of nucleic acid aptamers is generally categorized into three classes: (1) stem loop, (2) stem bulge, and (3) pseudoknot. A nucleic acid aptamer of the present invention preferably comprises a nucleotide sequence that forms a non-stem structure, such as, loop, bulge, or non-Watson-Crick type base pair in the vicinity of the complementary nucleotide sequence; and the non-stem structure constitutes a ligand-binding site or a part thereof. As used herein, the term "non-stem structure" refers to all conformations except the stem consisting of the Watson-Crick type base pair (B-type DNA). More specifically, a nucleic acid aptamer of the present invention preferably has a stem-junction structure, and binds to a ligand at the junction moiety. The stem-junction structure is a structure comprising both of the stem loop structure and stem bulge.

On the other hand, a ligand of the present invention can be any component other than nucleic acids that can be bound to the three-dimensional structure of a nucleic acid aptamer. Specifically, nucleic acid aptamers that exhibit the binding affinity for various low-molecular-weight compounds in addition to proteins have been reported. Previously reported ligands for nucleic acid aptamers are listed below:

Amino acids (Proc. Natl. Acad. Sci. USA 90, 3680-3684, 1993);

Nucleotides (Nature 364, 550-553, 1993; Biochemistry 34, 656-665, 1995);

Coenzyme A (Biochemistry 37, 4653-4663, 1998);

Theophylline (Science 263, 1425-1429, 1994);

Aminoglycosidic antibiotics (Biochemistry 35, 12338-12346, 1996);

Organic dyes (Nature 355, 850-852, 1992); and

Porphyrin derivatives (Biochemistry 35, 6951-6922, 1996).

Some proteins and dyes are known to bind to double-stranded nucleic acids. Some proteins, such as MutS, recognize mismatches in double-stranded nucleic acids and bind to them. The ligands of the present invention do not include ligands that recognize a structure consisting of only a pair of complementary nucleotide sequences. Known nucleic acid aptamers binding to such ligands can be used in the method for detecting nucleic acids of the present invention. Further, as described hereinafter, the present inventors discovered that cholic acid are trapped by a three-way junction constituted by nucleic acids as a ligand. A structure formed by the nucleotides indicated with boldface letters in FIG. 2, is the three-way junction (or three-stem junction). The term "three-way junction" refers to a structure where three double-stranded nucleic acid chains intersect at a single point as a result of the double-strand formation between the three nucleic acid chains. Specifically, three stems (double-stranded chains) intersect one another at a single point, and three complementary base pairs consisting of six nucleotides form the three-way junction. The three nucleic acid chains may be a single-stranded nucleic acid comprising stem-and-loop structure (FIG. 6*b*), or alternatively it may be formed by three independent nucleic acid chains (FIG. 6*a*).

Further, a structure wherein a single strand comprising a stem loop is hybridized to another single strand to form two stems (i.e., arbitrary two nucleic acid chains of the three chains in FIG. 6*a* form a loop) can be mentioned. Although tRNAs or the like are known to form a similar structure, the present inventors discovered for the first time that the junction region captures a ligand. The nucleic acid aptamer having the novel structure is one of preferred nucleic acid aptamers that can be used in the method for detecting nucleic acids of the present invention.

In order to use a nucleic acid aptamer for detecting a target nucleotide sequence, the aptamer is designed so that the mark structure of the nucleic acid aptamer changes depending upon the presence or absence of the target nucleotide sequence, which results in the change of the binding affinity for a ligand. For example, the nucleic acid aptamer that comprises the above-described three-way-junction structure newly found by the present inventors require all the three base pairs formed in the junction moiety to be perfectly complementary to each other to ensure the binding of the ligand. Furthermore, to obtain a higher affinity, two of the three base pairs in the junction are preferably G-C pairs. Since either of the two pairs can be provided within a probe, the remaining pair should be formed utilizing the G or C residues in the target nucleotide sequence. In other words, to detect a target nucleotide sequence according to the present invention, it is preferable to design the probe so that the junction is formed at the G or C residue in the target nucleotide sequence and the part of the probe corresponding to the junction is a G-C pair.

Alternatively, when a part of the target nucleotide sequence consisting of a sequence of G and C (i.e., GG, GC, CG, or CC) can be used as the nucleotides constituting the junction, the nucleotides of the probe constituting the junction may be an arbitrary Watson-Crick-type base pair. As a matter of course, if possible, a high affinity can be undoubtedly obtained by adopting G-C pairs for all the three base pairs of the junction.

Furthermore, it has been established that a higher affinity can be obtained by making the two strands constituting the stem part completely complementary to each other. On the other hand, the nucleotides of the loop moiety exert almost no influence on the affinity. Thus, the binding activity for the ligand serves as an index to assess the existence of a target nucleotide sequence, when the requirement for maintaining the affinity of the binding activity depends on the existence of the target nucleotide sequence.

Specifically, any one of the three DNA chains constituting the three-way junction is provided as the target nucleotide sequence and the remaining two are provided as probes; thus, the stem junction can be formed only when the target nucleotide sequence and the probe hybridize to each other. For example, a probe, which contains a stem-loop structure and complementary nucleotide sequences required for the hybridization with a target nucleotide sequence in the single-stranded moieties flanking the stem-loop structure, provides a three-way junction by hybridizing with the target nucleotide sequence. In other words, it is a T-shaped probe that comprises an intramolecular double-stranded structure formed by the complementary nucleotide sequences in the central portion between single-stranded DNAs and the two flanking single-stranded moieties that consist of nucleotide sequences complementary to the target nucleotide sequence. When such probes are used, the three-stem-loop structure consists only one loop which is formed within the probe. However, as confirmed in Example, the nucleotides of loop portions of the three-stem-loop structure don't influence the binding affinity for a ligand. Thus, the loop is not essential for acquiring the binding affinity of a ligand.

Preferred structures of the probes that can form a nucleic acid aptamer due to the hybridization with a target nucleotide sequence according to the present invention are indicated below:

probe A: –[T1]+[C]–[c]+[T2]–
probe B: –[T1]+[C]– and –[c]+[T2]–

Herein, [T1] and [T2] indicate nucleotide sequences complementary to the nucleotide sequences adjacent to a target nucleotide sequence. [C] and [c] are nucleotide sequences that are complementary to each other. The mark "+" indicates that no intervening nucleotides are permitted to be present in the region between the regions indicated on the right and left of "+". On the other hand, arbitrary intervening nucleotide sequences can be present for the region marked with "–". When compared with probe A, probe B lacks the [C]–[c] linkage in probe A; and consists of two separate oligonucleotide molecules. A probe having such a structure forms a junction when three stems intersect one another by hybridizing at the complementary nucleotide sequence in the presence of a target nucleotide sequence. According to the present invention, a probe having the following structure can be used as a probe that constitutes the nucleic acid aptamer.

–[T1]+[T2]–

[T1] and [T2] represent nucleotide sequences complementary to the nucleotide sequences adjacent to the complementary nucleotide sequence that can form a stem structure in the target nucleotide sequence. Specifically, when the target nucleotide sequence itself contains a pair of complementary nucleotide sequences to allow self-hybridization within the molecule, nucleotide sequences complementary to the nucleotide sequences adjacent to the 3' and 5' of the pair of complementary nucleotide sequences can be chosen as regions to which [T1] and [T2] hybridize, respectively.

In order to detect SNP in a target nucleotide sequence using the nucleic acid aptamer with the three-way-junction structure, the probe is designed so that the SNP to be detected is located in the very region corresponding to the three-way junction. The nucleic acid aptamer with such a structure allows to establish a reaction system where the binding affinity for a ligand is distinctively changed depending on the presence of SNP. By the use of a nucleic acid aptamer having the three-way-junction structure of the present invention, one can utilize the characteristic structure wherein the ligand-binding affinity is substantially lost, compared with the case where the base pair of the junction moiety is perfectly complementary, as a result of a mismatch due to SNP in a base pair. High accuracy and sensitivity can be expected by the nucleic acid aptamers whose binding affinity is considerably altered depending on the difference of a single-nucleotide.

According to the present invention, hybridization of a probe with a target nucleotide sequence is detected using ligand-binding affinity as an index. Any of the known principles of binding assay is applicable to the binding of a nucleic acid aptamer to the ligand. Some detection principles are specifically described below.

Inhomogeneous System:

A nucleic acid aptamer, which is formed by the hybridization between a labeled probe and a target nucleotide sequence, can be trapped by a ligand on a solid phase. The detection of the target nucleotide sequence is achieved by detecting the labeled probe trapped on the solid phase (or remaining in the liquid phase). The step of trapping the labeled probe onto a solid phase according to the present invention is a common step with known nucleic acid hybridization assays. However, the binding to the solid phase according to the present invention is based on a different principle from that of the hybridization between complementary nucleotide sequences, and thus allows the use of much more efficient washing conditions. That is, according to the method of the present invention, one can readily select a condition ensuring sufficient removal of the labeled probe that is non-specifically adsorbed on the solid phase or bound to the ligand, even when the wash is carried out under conditions of lower stringency exerting no influence on the complementary base pairing. This enables specific detection with lower background signals.

Homogeneous System:

Binding of a molecule with a fluorescent substance has been known to give fluorescence polarization. Utilizing this phenomenon, the method for detecting target nucleotide sequences of the present invention can be performed in a homogeneous system. Specifically, a target nucleotide sequence can be detected by first labeling a probe or ligand with fluorescence; and then detecting fluorescence polarization that is generated because of the binding of the nucleic acid aptamer and a ligand. Known fluorescent labels include fluorescein isothiocyanate, etc. A compound emitting fluorescence can also be used as the ligand. For example, one of the known ligands binding with a nucleic acid aptamer includes porphyrin derivatives many of which emit fluorescence.

Surface Plasmon Resonance:

The surface plasmon resonance (SPR) method is known as a technology to optically detect the binding of substances in a direct way. The surface plasmon resonance (SPR) sensor detects the interaction of biological molecules based on the alterations in the refractive index of medium near a thin metal film. SPR occurs when the surface plasmon is excited at the metal/liquid boundary (sensor surface). The other surface avoid of the sample is exposed to light and the reflected light from the surface is detected. The intensity of the reflected light is decreased according to the specific combination of angle and wavelength depending on the SPR (generation of SPR signal). The refractive index near the surface is altered due to the presence of molecules bound to the sensor surface; the alterations can be observed as changes in the SPR signal. Further alterations in the refractive index and SPR signal result from the interaction of biological molecules. The interaction of biological molecules can be measured by detecting such signal alterations.

According to the method for detecting nucleic acids of the present invention, by immobilizing ligands trapped by a nucleic acid aptamer on a chip, the amount of the nucleic acid aptamer generated by the hybridization between a target nucleotide sequence and a probe can be determined based on the changes in the SPR signal. The target nucleotide sequence used for the hybridization with the probe may be amplified products obtained by amplification methods, such as PCR. Methods for immobilizing ligands on a chip include the avidin-biotin reaction, but are not limited thereto. The use of SPR enables a high sensitive detection without any labeling substance.

Both the nucleic acid molecules (which serve as a target nucleotide sequence) and the probe of the present invention may be any type of nucleic acid molecules or derivatives thereof, so long as the two molecules can hybridize to form a nucleic acid aptamer. Specifically, such molecules include natural or chemically synthesized nucleic acid molecules, such as RNA and DNA; RNA or DNA derivatives consisting of synthetic nucleotide derivatives; derivatives whose backbone comprise peptide bonds or alkyl chains; etc. These nucleic acid molecules or derivatives thereof may be, beside those derived from biological samples, products obtained by enzymatic amplification reactions of nucleic acids, such as PCR and NASBA methods, using nucleic acid molecules derived from samples as templates.

The probes and ligands, which are necessary to perform the method for detecting a target nucleotide sequence of the present invention, can be pre-formulated as a kit. The method for detecting target nucleotide sequences according to the present invention can contain reagents required for detecting labels, control samples, and others.

All publications of prior arts cited herein are incorporated herein by reference in their entireties.

BRIEF DESCRIPTION OF THE DRAWINGS

FIG. 2 shows the predicted secondary structures of clones 1 (SEQ ID NO: 8) and 2 (SEQ ID NO: 9). The nucleotide sequences of the deletion mutants, ch-1-39 and ch2-38, containing the minimal sequence required for the binding of each clone with cholic acid are italicized. The nucleotide sequences of the deletion mutants, ch1-47 and ch2-40, which contain the entire three-way junction region, are indicated with outlined letters.

FIG. 4 depicts the predicted secondary structures of deletion mutants, clones 5 (Residues 7-69 of SEQ ID NO: 10), 7 (Residues 27-95 of SEQ ID NO: 11), 9 (Residues 23-70 of SEQ ID NO: 12), and 11 (Residues 1-76 of SEQ ID NO: 13), which contain a three-way-junction region. The arrow indicates the minimal nucleotide sequence required for the binding of clone 5 or 9 to a cholic acid-immobilized column.

FIG. 5 depicts the result of mutation analysis of ch2-40 (SEQ ID NO: 7). Mutations were introduced to ch2-40 by (a) base pair substitution, (b) single-nucleotide substitution, or (a) deletion/insertion. The substituted or deleted nucleotides are indicated with boldface letters. The arrow and number indicate the nucleotide to be substituted or deleted and the percentage of affinity of a mutant ch2-40 to the non-mutated ch2-40, respectively.

Figure 1:
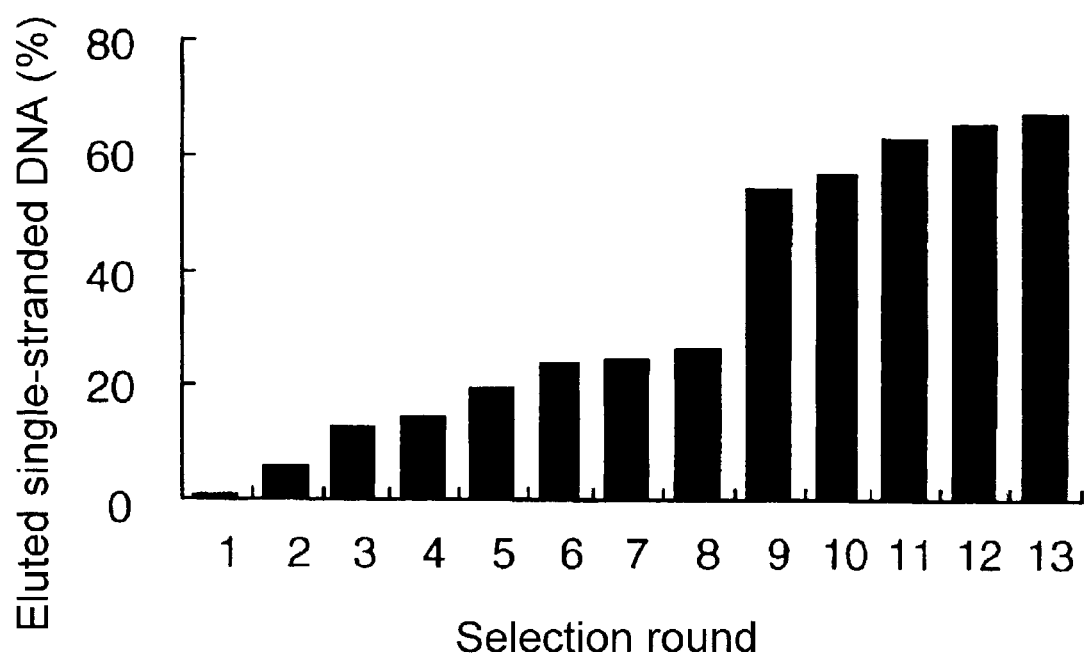
FIG. 1 is a diagram demonstrating the percentage of eluted single-stranded DNA in each selection round. The ordinate indicates the percentage of the eluted DNA to the loaded DNA, and the abscissa indicates the number of rounds.

lane 1: control nucleic acid that was denatured to a single strand;
lane 2: ch9-48, without cholic acid;
lane 3: ch9-48, with cholic acid;
lane 4: ch9-48-C6, without cholic acid;
lane 5: ch9-48-C6, with cholic acid; and
lane 6: A+G ladder of ch9-48 obtained by the Maxam-Gilbert method.

Figure 8:
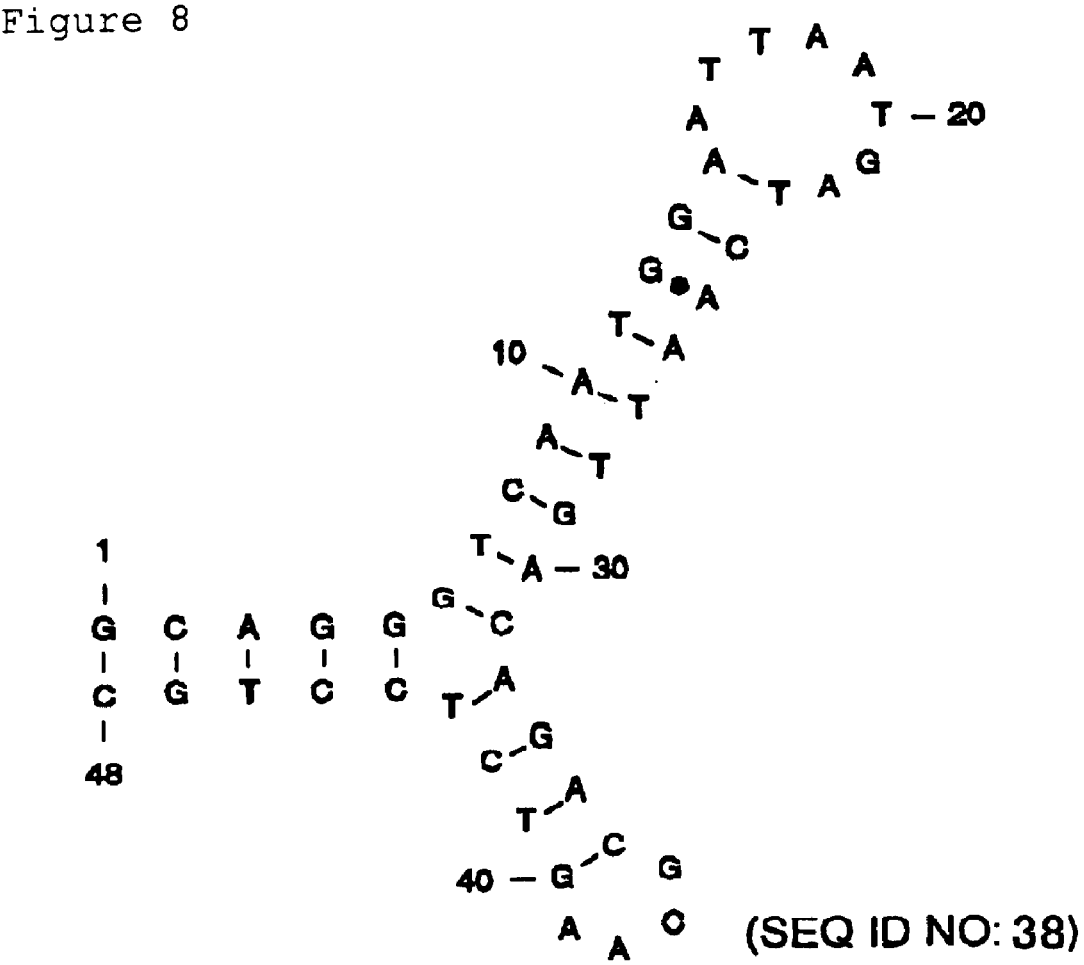

FIG. 8 depicts the predicted secondary structure of ch9-48 (SEQ ID NO: 38). Thymine (T) is indicated with boldface letters.

FIGS. 9-21 depict the source code list of the software program used in the Example for selecting nucleotide sequences forming a nucleic acid aptamer of the present invention.

BEST MODE FOR CARRYING OUT THE INVENTION

The present invention is specifically illustrated below with Examples.

EXAMPLE 1

Selection of DNA Aptamers that Bind to Cholic Acid by the SELEX Method (1) Procedure for Selecting DNA Aptamers Binding to Cholic Acid DNA aptamers that specifically bind to cholic acid were selected from a single-stranded DNA (hereinafter abbreviated as "ssDNA") pool containing single-stranded 100-mer oligonucleotides, which include random inserts of 64 nucleotides (5'-GTACCAGCTTATTCAATT-$N_{64}$-AGATAGTAT-GTTCATCAG-3'; SEQ ID NO: 1) ($N_{64}$ represents a random sequence with 64 nucleotides), by the SELEX method (Nature 355, 564-566, 1990). The single-stranded DNA library contained about $9 \times 10^{14}$ independent sequences. The ssDNAs were synthesized by the phosphoamidate method, and were purified by high-performance liquid chromatography. The 100-mer DNAs were purified by solid-phase extraction using reverse-phase resins.

Each round of the selection was conducted as follows. First, a 100 mer single-strand oligonucleotide with a random insert of 64 nucleotides was denatured in selection buffer (50 mM Tris-HCl, 300 mM NaCl, 30 mM KCl, 5 mM $MgCl_2$, pH 7.6) at 95° C. for 5 min, and then allowed to cool slowly to room temperature. The folded ssDNA (45 μg in the first cycle, and 2 to 3 μg in the subsequent cycles) in the selection buffer was loaded onto 500 μl cholic acid-agarose column (2 μmol cholic acid/g gel; SIGMA; hereinafter, abbreviated as selection column), which had been equilibrated with more than 10 ml of the selection buffer. After equilibration for 30 min, the column was washed with 5 to 10 column volumes of the selection buffer. The remaining ssDNA was eluted with 1.5 ml selection buffer containing 5 mM cholic acid, collected, and then precipitated with ethanol in the presence of 20 μg/ml glycogen. The amount of specifically eluted ssDNA with 5 mM cholic acid was estimated by UV absorbance of the collected fractions at 260 nm. The ssDNA was amplified by polymerase chain reaction (PCR).

Affigel 102, on which cholic acid had been immobilized in place of cholic acid-agarose, was used in selection rounds 10 and 12 to eliminate the ssDNAs which bind to the aminohexyl linker of cholic acid-agarose. The immobilization of amino ethyl linker through cholic acid to Affigel 102 was conducted as follows:

20 mg cholic acid was coupled to 3 ml Affigel 102 with 100 mg EDC as the condensing agent in 10 ml of 20 mM HEPES (pH 7.5). The mixture was incubated at room temperature for 10 hr with occasional agitation. The concentration of cholic acid on Affigel 102 (8 μmol/ml gel) was determined by the reaction with 2,4,6-trinitrobenzene sulfonic acid. The cholic-acid immobilized Affigel 102 was mixed with 3 volumes of Affigel 102 to adjust the concentration of cholic acid in the column approximately 2 μmol/ml.

Counter selections were also done, after selection rounds 5, 6, 7, and 13, to remove the ssDNAs that bind directly to agarose matrix. More specifically, ssDNA was loaded on the Sepharose 4B control column (SIGMA) to remove the ssDNAs bound to the agarose matrix.

(2) Amplification by PCR

PCR was carried out using the primers 5'-biotin-CTGAT-GAACATACTATCT-3' (SEQ ID NO: 2) and 5'-GTAC-CAGCTTATTCAATT-3' (SEQ ID NO: 3). 100 μl PCR mixture, which contains 1 unit of Ex Taq DNA polymerase (TaKaRa), 60 pmol of each primer, 20 nmol of each dNTP, and 0.4 to 0.8 μg of Perfect Match (*E. coli* ssDNA binding protein) (Stratagene), was added to improve the fidelity of the polymerase reaction. The thermal cycling for PCR was 94° C. for 30 sec, 46° C. for 30 sec, and 72° C. for 30 sec. The amplified biotinylated double-strand DNA was extracted with phenol/chloroform, precipitated with ethanol, and bound to the avidin immobilized on column for the generation of ssDNA. The obtained ssDNAs were used as the input for the subsequent selection round. These steps were repeated to enrich the ssDNAs having the binding affinity for cholic acid.

(3) Cloning and Nucleotide Sequence Analysis

The PCR products of double-stranded DNA amplified from the library of selection round 13, were cloned into pGEM-T vector (Promega) to determine their sequences by the dideoxy method. Sequence homology analysis and prediction of the secondary structures of ssDNAs according to the free energy minimization method were achieved by the MacDNASIS Pro v1.0 program (HITACHI Software Engineering). Search for complementary sequences forming three stems in each sequence clone was carried out with original computer program written by the C language. FIGS. 9-21 show the source code list for the computer program. Further, the algorithm of the computer program is summarized below.

This algorithm determines all potential three-way-junction structures in a given nucleotide sequence. As described above, a three-way-junction structure represents a structure containing stem 1, stem 2, and stem 3 that intersect at a single point (FIG. 8). According to the algorithm, first, possible nucleotide sequences forming stem 1 are assessed by repeating the search for complementary nucleotide sequences. In the next step, when stem 1 could be formed, then the search for a nucleotide sequence that can form stem 2 is carried in the remaining region. When the stem 2 could also be formed, then the search for a nucleotide sequence that can form stem 3 is carried out in the remaining region. Each step of the search is carried out as follows:

1) Determining Potential Stem 1.

Search is started from the 5'-end of a given nucleotide sequence, and proceeds toward the 3'-end, nucleotide by nucleotide. Each nucleotide is taken as the starting point of stem 1, which is referred to as stem 1b, and the possibility of stem 1 formation are assessed as follows. Specifically, a nucleotide sequence complementary to the stem 1b is searched starting from the 3'-end, and the complementary nucleotide is referred to as stem 1e, the terminal residue of the stem 1. When a nucleotide sequence, with the same length, of "minimal stem length" from the stem 1b toward the 3'-end direction is complementary to the nucleotide sequence starting from the stem 1e extending toward the 5'-end direction, the stem 1 is assumed to be formed. The "minimal stem length" may be any arbitrary value.

2) Obtaining Potential Stem 2 as Follows.

Whether a stem 2 can be formed in the sequence of the region excluding those corresponding to the stem 1 is determined by the same method as in the above 1). However, it is necessary that the length of loop portion in the stem 2 has the "minimal loop length" or longer. Further, the stem 2b, the starting position of stem 2, is selected so that the distance between the stem 2b and the stem 1 is the "gap size" or shorter. The "minimal loop length" and "gap size" can be any arbitrary values.

3) Obtaining Potential Stem 3 as Follows.

Whether a stem 3 can be formed in the sequence of the region excluding those regions constituting stem 1 and stem 2 is determined by the same method as in the above 2). However, the starting position of stem 3, stem 3b, and the termination position of stem 3, stem 3e, are selected so that the distance between the stem 3b and the stem 2, as well as the distance between the stem 3e and the stem 2 are the above described "gap size" or shorter.

(4) Experimental Result

After the first round of selection as described above, 1% or less of the ssDNAs loaded were trapped on the selection column. In the subsequent rounds, the quantity of ssDNAs bound to cholic acid markedly increased. In the selection round 13 and later rounds, about 70% of the loaded ssDNAs was trapped on the column, and were then eluted (FIG. 1).

After round 13, the nucleotide sequences of 19 clones were determined to define a common motif sequence responsible for the binding with cholic acid. The sequences of the 19 clones were entirely different from one another, and no significant homology could be detected among the sequences by primary sequence homology search using the MacDNASIS program. However, as depicted in Table 1, sequences presumed to form three-way junctions as a secondary structure were observed. Three pairs of three-way regions (regions constituting the double-stranded chain) are underlined, indicated with boldface letters, and indicated with outlined letters, respectively, in the nucleotide sequences demonstrated in Table 1. The italicized letters indicate mismatched or wobble (T-G) position in the stem region.

TABLE 1

| Clone | Sequence | |
|---|---|---|
| a) | | |
| 1 | 5'-GTACCAGCTTATTCAATTACAGATCGAGGCAGCGATAGTGGGCTAA TAAGGTTAGCC CCATCGGTCCTGGACTTGGGACTAGATATGTTCATCAG-3' | SEQ ID NO: 8 |
| 2 | 5'-GTACCAGCTTATTCAATTAGCCGCCGATTGACCCAAATCGTTTTG TATGCAAAA GCGCTGCTGTATCAACTGTTACCATGAAGATATGTTCATCAG-3' | SEQ ID NO: 9 |
| 5 | 5'-GTACCAGCTTATTCAATTCGGCGAAGACGAATTCCAAG CCGCGCGGGTCACGCGACTTGG GAATGAGCAAGGTTGGCCCGAGATATGTTCATCAG-3' | SEQ ID NO: 10 |
| 7 | 5'-GTACCAGCTTATTCAATTGGGCGAAG GAACATACGGCAGTTTATGCCGCTATC GAGATAGACTATCATCTCAACGTCTTCTA GATAG TATGTTCATCAG-3' | SEQ ID NO: 11 |
| 9 | 5'-GTACCAGCTTATTCAATTGCGA GCAGGGTCAATGAATTAATGATCAATTGACAGAC GCAAGTCT CCTGCGGTCCTGTGTTGAGATATGTTCATCAG-3' | SEQ ID NO: 12 |
| 11 | 5'-GTACCAGCTTATTCAATTCAATTACACCGACAGAGGTAGCGCTCTCGCCATTGAGTT GCTGCGGGC TGAAGCCCG GTACATGGAGATAGTATGTTCATCAG-3' | SEQ ID NO: 13 |
| b) | | |
| 3 | 5'-GTACCAGCTTATTCAATTA GGGATCGGACGTGAGGCCGATAGGCCGAAACGTCAAG GGTGAGAGTAAGGAGGG CTT CGATTCCAGATAGTAGTTCATCAG-3' | SEQ ID NO: 14 |
| 4 | 5'-GTACCAGCTTATTCAATTCAATTGGACGTAGGCGAAGAGTTGGCGGAGTTAGGATT TTGAAGAAGGCTAA ACACCTTAGC CTGGGACTAGAGATAGTATGTTCATCAG-3' | SEQ ID NO: 15 |
| 6 | 5'-GTACCAGCTTATTCAATTCAATTACCGCGAAGAAGTGTCATTGTTTTGGAGATTCGAA GCGCTG TACACAG GTAATGAAGCCTTCTAAGATAGTATGTTCATCAG-3' | SEQ ID NO: 16 |
| 8 | 5'-GTACCAGCTTATTCAATT ACAACGGAGGCCAAGGGACTCCC ACGCT TTTTATACG GGG CGATGTTTGAGAAGTCTCCCACGAGATAGTATGTTCATCAG-3' | SEQ ID NO: 17 |
| 10 | 5'-GTACCAGCTTATTCAATTCGA CAACGAGGGGCCGAGTATCCGAAA TTGGCGGC GTAAAGCAATTGTAGTTAAGCTCTCATGTAGATAGTATGTTCATCAG-3' | SEQ ID NO: 18 |
| 12 | 5'-GTACCAGCTTATTAT TCAATTGCCACCCGAGGTGCGA AACGGGG TACGAAACAATTCAG CCCGT CTCG GCATTTGACTTGCGTTGCGTTAAGATATGTTCATCAG-3' | SEQ ID NO: 19 |
| 13 | 5'-GTACCAGCTTATTC CAATTGGGAACGATGAATTATTCGGGCCCTGAGTT GTTAGAACTCAG GTTAATTTCAGTCTCTTACGATTGCCGCCGAGTGTGAGATAGTATGTTCATCAG-3' | SEQ ID NO: 20 |
| 14 | 5'-GTACCAGCTTATTC AATTAGTTCAACTGGAGGTTGGTC GCAAGAC ACTAACTTCAGTCTTCTTACGATTGCCTTAGATAGTATGTTCATCAG-3' | SEQ ID NO: 21 |
| 15 | 5'-GTACCAGCTTATTT CAATTGCCCGGGATGTGAACGGAACGGCGATAA CTTAGTTTTATCG GCAGTTGGATGGAATGTCGCCTTAGATAGTATGTTCATCAG-3' | SEQ ID NO: 22 |
| 16 | 5'-GTACCAGCTTATTCAATTG GCAGCCGGACTACCAGGCCGGATG ACGTTAGGCGACACATC CTGCTTATAAGCTTATGTCGTAGATAGTATGTTCATCAG-3' | SEQ ID NO: 23 |
| 17 | 5'-GTACCAGCTTATTCAATTG GGGTTGTAACAGGCAATTAGACGA CAATTGGGCAG CATTCTGCC AATAAGTATGTTATTGAGATAGTATGTTCATCAG-3' | SEQ ID NO: 24 |
| 18 | 5'-GTACCAGCTTATTCAATTCGACGCAGAAGATA AATAACAGCAG ACTTCCTGCTG GCTCGGCTTTCCGCTCATCTTCGCCAAGATAGTATGTTCATCAG-3' | SEQ ID NO: 25 |
| 19 | 5'-GTACCAGCTTATTCAATTACGTCGAAAGGTTTC GGCGAGAGGGGCATCAAGTGCCGCTC ATAGAGC CTCGAGTCCATACCCTGAGATAGTATGTTCATCAG-3' | SEQ ID NO: 26 |

EXAMPLE 2

Search for Cholic Acid Binding Motif Sequences Using Deletion Mutants of Various DNA Aptamers (1) Dissociation Constant Determination The affinity of cholic acid with ssDNAs was analyzed by the equilibrium-filtration method (Science 263: 1425-1429, 1994). Cholic acid was added to the DNA samples in the selection buffer (200 µl) at a final concentration of 50 µM. Each binding mixture was incubated at 25° C. for 5 min. The mixture was then placed in Microcon 10 filtration device (Amicon) and centrifuged for 15 min at 850×g. Cholic acid that is not bound to the ssDNAs can be recovered as the filtrate by this procedure. The concentrations of cholic acid in 20 to 30 µl of filtrate were determined by diagnostic kit (WAKO chemical) for quantitative determination using 3α-hydroxysteroid dehydrogenase and diaphorase including p-nitrotetrazolium blue dye and nicotinamide adenine dinucleotide. For each ssDNA sample, the concentration of bound cholic acid ($C_b$) was determined by the difference of cholic-acid concentration between the filtrate and retentate, which was calculated by the following equation (equation 1):

$$C_b(\mu M) = C_r - C_f = (10000 - V_f \times C_f)/(200 - V_f) - C_f$$

(wherein, $V_f$(µl) is the volume of filtrate; and $C_r$ and $C_f$(µM) represent the concentrations of cholic acid in the retentate and filtrate, respectively).

The equilibrium-dissociation constants ($K_d$) were calculated from the following standard quadratic binding equation (equation 2):

$$C_b = (1/2)\{D_t + 50 + K_d - [(D_t + 50 + K_d)^2 - 200 D_t]^{1/2}\}$$

(wherein, $D_t$ is the total concentration of ssDNA)

(2) Determination of the Affinity (Binding Constant) of Various DNA Aptamer Deletion Mutants for Cholic Acid To determine the minimal sequence required for the binding with cholic acid, the present inventors prepared a series of deletion mutants derived from clones 1 and 2 by truncating one or more nucleotides from the 5'- and 3'-ends of the full-length aptamers. 0.5 nmol of clone 1, clone 2, and each of the deletion mutants, was applied to selection column, and the amount of ssDNA specifically eluted from the selection column with 5 mM cholic acid was measured (75% and 77% of clones 1 and 2, respectively, was specifically eluted). According to an experiment using the 39mer deletion mutant of clone 1, ch1-39 (5'-GAGGGCAGCGAT-AGCTGGGCTAATAAGGTTAGCCCCATC-3'; SEQ ID NO: 4), and the 38mer deletion mutant of clone 2, ch2-38 (5'-GCGCCGATTGACCCAAATCGTTTTGTAT-GCAAAAGCGC-3'; SEQ ID NO: 5), the deletion mutants were determined to correspond to the minimal sequences essential for the binding with cholic acid. 22% and 40% of ch1-39 and ch2-38, respectively, were eluted from the selection column. However, no elution could be observed for deletion mutants with shorter sequences. Interestingly, the secondary structures of clones 1 and 2 predicted by the MacDNASIS program had a structure formed by the binding of three stems with more than 4 base pairs, and both ch1-39 and ch2-38 included this "three-way-junction" region (FIG. 2).

Figure 3:
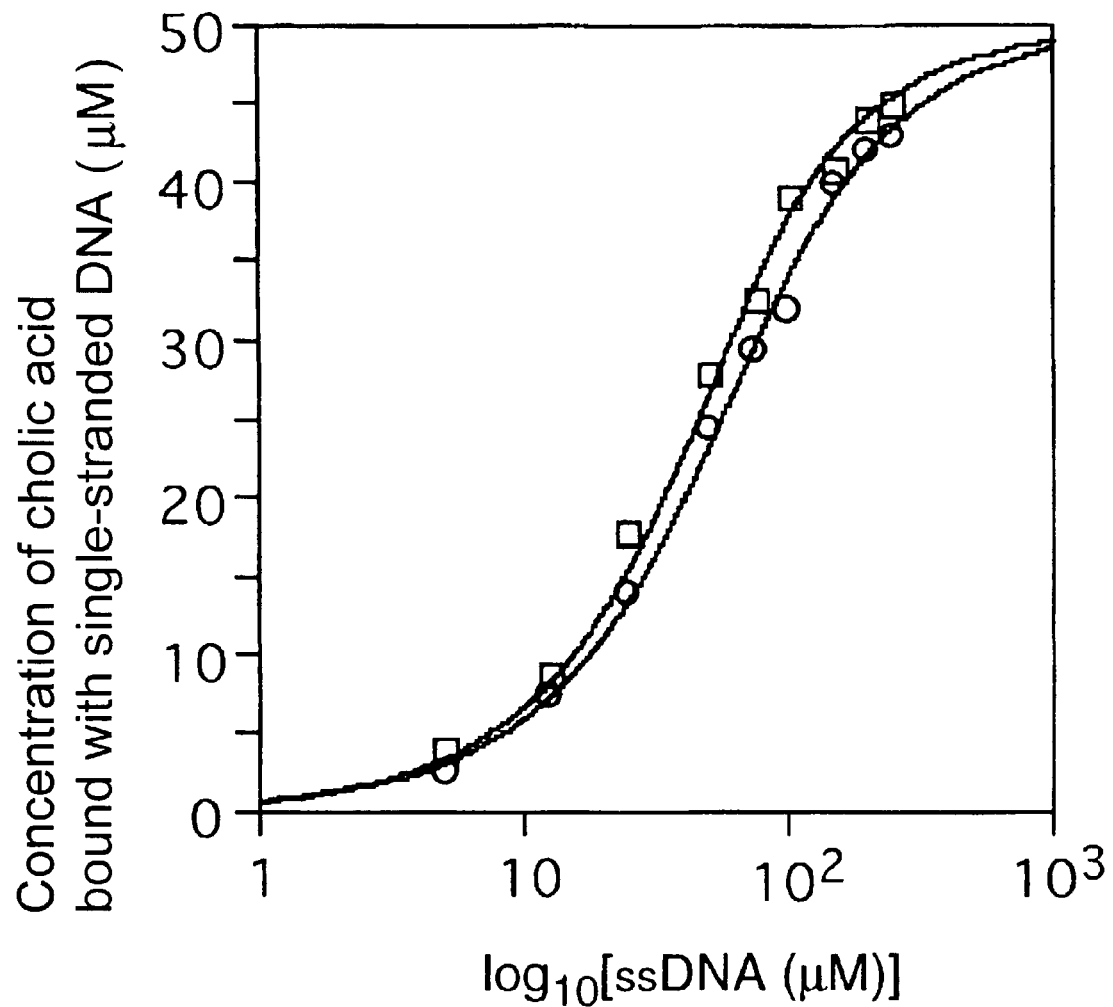
FIG. 3 is a diagram showing the cholic acid-binding curves for ch1-47 (open circle) and ch2-40 (open square). The ordinate indicates the concentration ($\mu$M) of cholic acid bound to the single-stranded DNA, and the abscissa indicates the concentration of single-stranded DNA ($\mu$M) in logarithmic scale.

Then, the present inventors prepared deletion mutants of clones 1 and 2, which included the intact sequences of this region, and dubbed them ch1-47 (5'-GATCGAGGGCAGC-GATAGCTGGGCTAATAAGGTTAGCCCCCATCGGTC-3'; SEQ ID NO: 6) and ch2-40 (5'-AGCGCCGATTGAC-CCAAATCGTTTTGTATGCAAAAGCGCT-3'; SEQ ID NO: 7), respectively. The affinity for cholic acid of these mutants was measured (FIG. 3). These mutants exhibited an affinity for the selection column that was almost the same as those of full-length clones (70% and 73%, respectively). From equation 1 and 2, and the results in FIG. 3, the dissociation constants ($K_d$) for cholic acid were determined as 31.0 µM and 19.6 µM for ch1-47 and ch2-40, respectively. Furthermore, among the predicted secondary structures of 17 other sequenced clones with full-length sequences, 4 clones (clones 5, 7, 9, and 11) included a three-way junction similar to that of ch2-40 (FIG. 4). Deletion mutants, ch5-63, ch7-69, ch9-48, and ch11-76, containing the intact three-way-junction regions of these 4 clones were prepared to determine the dissociation constants thereof for cholic acid (Table 2).

TABLE 2

| Clone name | Dissociation constant (µM) |
|---|---|
| ch5-63 | 28.7 |
| ch7-69 | 16.7 |
| ch9-48 | 5.0 |
| ch11-76 | 52.1 |

The affinity of clones 5 and 9 for the selection column was completely lost by the deletion of a few nucleotides from the 5'- and 3'-ends of the three-way-junction region.

The predicted secondary structure of clone 11 was more complex than the other 5 clones. A 35mer mutant oligomer of clone 11 was prepared by truncating nucleotides except those of the three-way-junction region to determine the dissociation constant for cholic acid. As a result, the dissociation constant was demonstrated to be 76.8 µM, which is comparable to that of the 76mer deletion mutant (52.1 µM).

By comparing the predicted three-way-junction structures of the 6 clones described above, two common features emerged. First, a high affinity is provided when the 3 stems and 2 loops are constituted of 4 base pairs or more. Second, the affinity is elevated by constituting the 3 base pairs flanking the junction with 2 or 3 GC base pairs.

Furthermore, the sequences of another 13 clones were analyzed with computer program based on the above-mentioned algorithm. The condition for analysis by the program was as follows. First, each sequence was searched with the requirement that the minimal stem-2 length is 2, minimal loop length is 4, and gap size is 0. Then, nucleotide sequences, whose junction moiety contains two or more GC base pairs and at the same time whose stems of the three-way junction constitute of 3 base pairs or are longer, were selected visually (namely, without using any program) from the nucleotide sequences that meet the requirement. At this stage, the stem was permitted to contain mismatches. Namely, like ch1-47 the sequences were permitted to contain mismatches in the third and subsequent base pairs from the junction in the stem. In such cases, mismatches are not counted as the stem length. Thus, sequences whose length of each stem was 3 base pairs or longer excluding mismatched base pairs was selected. As a result, 12 clones comprising of sequences that contain the three-way-junction structure; each contained stems having 3 or more base pairs, and 2 or 3 GC base pairs were present near the junction. The remaining 1 clone also comprised a sequence containing the three-way-junction structure while one of the three stems contained only 2 base pairs. Deletion mutants of the 13 clones, which contained the normal three-way junction region, were prepared, and their affinity for cholic acid was tested. Table 3 shows the nucleotide sequences of these deletion mutants of the 13 clones and the above-mentioned 6 clones. These nucleotide sequences correspond to those existing between the nucleotide sequences underlined in the nucleotide sequences indicated in Table 1.

Table 3. Table discloses SEQ ID NO: 6-7 and 32-48, respectively, in order of appearance TABLE 4-continued

| Clone name | Dissociation constant (μM) |
|---|---|
| ch15-54 | 67.5 |
| ch16-40 | 10.7 |
| ch17-63 | 23.4 |
| ch18-56 | 36.6 |
| ch19-40 | 40.5 |

TABLE 3

Table discloses SEQ ID NO: 6-7 and 32-48, respectively, in order of appearance

| Aptamer | Type of the junction | Sequence |
|---|---|---|
| ch1-47 | 3G-C | 5'-GATCGAGGGCAGCGATAGCTGGGCTAA TAAGGTTAGCC CCATCGGTC-3' |
| ch2-40 | 2G-C | 5'- AGCGCCGATTGACCCAAATCGTTTTG TATGCAAAA GCGCT-3' |
| ch3-63 | 2G-C | 5'-GGGATCGGACGTGAGGGCGATAGGCGAA ACGTCAAG GGTGAGAGTAAGGAGGGCTT CGATTCC-3' |
| ch4-74 | 3G-C | 5'-CCAGCTTATTCAATTGGACGTAGGCGAAGTTGGCGGAGTTAGGATT TTGAAGAAGGCTAA ACACCTTAGC CTGG-3' |
| ch5-63 | 2G-C | 5'-GCTTATTCAATTCGCGGAAGACGAATTCCAAG CGCGCGCGGGTCACGCGACTTGG GAATGAGC-3' |
| ch6-56 | 3G-C | 5'-ATTACCGCGAAGAAGTGTCATTGTTTTGGAGATTCGAA GCGCTG TACACAG GTAAT-3' |
| ch7-69 | 2G-C | 5'-GAACATACGGCAGTTTATGGCCGCTATC GAGA TAGACTATCATCTCAACGTCTTCT AGATAG TATGTTC-3' |
| ch8-47 | 3G-C | 5'-ACAACGGAGGCCAAGGGACTCCCACGCT TTTTATAGCG GGGCGATGT-3' |
| ch9-48 | 2G-C | 5'-GCAGGGTCAATGGAATTAATGATCAATTGACAGAC GCAAGTCT CCTGC-3' |
| ch10-52 | 2G-C | 5'-CAATTCGACAACGAGGGGCGGAGTATCCGAAATTGGCGGCGTAAAGCAATTG-3' |
| ch11-76 | 3G-C | 5'-GTACCAGCTTATTCAATTACACGGACAGAGGGTAGCGGCTCTGCGCATTGAGTT GCTGCGGGC TGAAGCCCG GTAC-3' |
| ch12-61 | 3G-C | 5'-TCAATTGCCACCGCGAGGTGCGA AACGGG TACGAAACAATTCAG CCCGT CTCG GCATTTGA-3' |
| ch13-53 | 3G-C | 5'-CAATTGGGAACGATGAATTATTCGGGCCCTGAGTT GTTAGAACTCAG CAATTG-3' |
| ch14-37 | 2G-C | 5'-ATTAGTCAACTGGAGGTTGGTC GCAAGAC ACTAATT-3' |
| ch15-54 | 3G-C | 5'-CAATTGCCCGGGATGTGGAACGGAACGGCGATAA CTTAGTTTTATCG GCAGTTG-3' |
| ch16-40 | 3G-C | 5'-GCAGCGGACTACAGGCCGGATG ACGTTAGCG ACATC CTGC-3' |
| ch17-63 | 2G-C | 5'-CTTATTCAATTGGGGTTGTAACAAGGCAATTAGACGA CAATTGGGCAG CATTCTGCC AATAAG-3' |
| ch18-56 | 2G-C | 5'-CCAGCTTATTCAATTCGACGCAGAAGATAAATAACAGCAG ACTTCCTGCTG GCTGG-3' |
| ch19-40 | 3G-C | 5'-GGCGAGAGGGCATCAAGTGCCGCTC ATAGAGC CTCGAGTC-3' |

The dissociation constants of the deletion mutants of the 13 clones for cholic acid are shown in Table 4. All of the deletion mutants bound to cholic acid.

TABLE 4

| Clone name | Dissociation constant (μM) |
|---|---|
| ch3-63 | 31.1 |
| ch4-74 | 15.6 |
| ch6-56 | 28.9 |
| ch8-47 | 12.6 |
| ch10-52 | 60.7 |
| ch12-61 | 12.2 |
| ch13-53 | 18.7 |
| ch14-37 | 6.4 |

All the 19 clones whose sequences had been determined contained the cholic acid binding sequence, which sequence was predicted to form the common secondary structure (i.e., the three-way junction).

EXAMPLE 3

Influences of Single-Nucleotide and Single-Base-Pair Mutations on the Cholic Acid Binding Affinity (1) Influences of Substitutions in the Stem or Loop on the Affinity In order to determine the important components responsible for the formation of predicted three-way-junction structure and the binding with cholic acid in the selected clones, the deletion mutant ch2-40, which contains the three-way-junction region of clone 2, was subjected for mutation analysis. A series of ch2-40 mutants, which contain single-nucleotide substitution, single-base-pair substitution, or single-nucleotide deletion or insertion, were synthesized. The relative binding affinity of each mutant for cholic acid was assessed by the "equilibrium-filtration method". FIG. 5a shows the binding affinity of the deletion mutant ch2-40, when the nucleotide has been substituted with the nucleotide indicated with an arrow. FIG. 5b shows the binding affinity of ch2-40, when a base pair forming the stem region of the three-way junction has been substituted with the base pair indicated by an arrow.

As shown in FIG. 5a, pairwise compensatory substitutions on the possible 3 stems from G-C to A-T base pair reduced the relative binding affinity 65.3% ($C_6$-$G_{21}$ to $T_6A_{21}$), but still demonstrated some affinity. In contrast, several single base-substitutions around the junction abolished the binding affinity completely (FIG. 5b; $G_4$ to $C_4$, $C_6$ to $G_6$, $A_{22}$ to $T_{22}$, and $G_{36}$ to $C_{36}$). Comparing the effect of single base and pairwise substitutions to the binding affinity, the former, which disrupt the proposed Watson-Crick base pair in the predicted secondary structure, reduced the binding affinity more significantly than the latter.

This result supports the formation of the predicted secondary structure and indicates the importance of the formation of the three-way-junction structure for maintaining the affinity. Both single base and base pair substitutions around the junction of ch2-40 significantly reduced the binding affinity, whereas those base and base pair substitutions near the 5'-end, 3'-end, and on the 2 loops did not decrease. Furthermore, single base substitutions on the 2 loops, as well as deletion of $A_{12}$ and $A_{28}$, and insertion of an adenosine between $A_{12}$ and $C_{13}$, or $A_{28}$ and $T_{29}$ hardly affected the binding affinity. In conjunction with the fact that no apparent similarity of the sequence and length of the stem and loop regions could be observed among the 19 clones, the binding site for cholic acid was indicated to be the junction of 3 stems.

Figure 6:
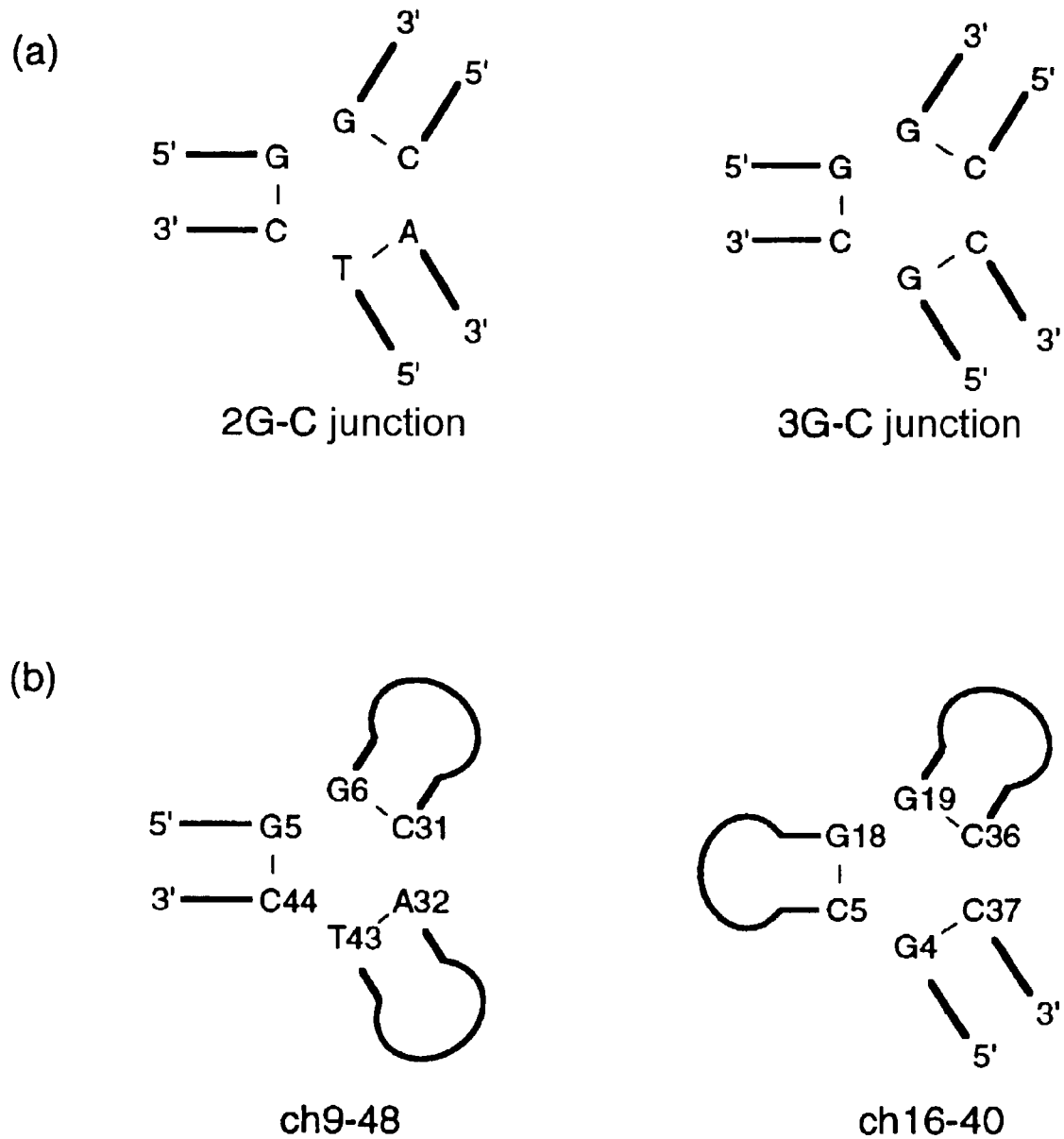
FIG. 6 depicts the structures of 2G-C junction and 3G-C junction. Panel (a) depicts a schematic illustration of the structure of each junction. Panel (b) depicts the structures of ch9-48 and ch16-40 as examples of the junctions.

(2) Influences on the Affinity of Substitutions of the Three Base Pairs in the Junction Next, the present inventors focused on the variation and arrangement of 3 base pairs in the junction of the selected 19 clones. The junctions of these clones consisted of either 2 G-C and 1 A-T, or 3 G-C base pairs (termed 2G-C and 3G-C junction, respectively) (FIG. 6a). 2G-C junction and 3G-C junction, ch9-48 and ch16-40, respectively, are represented in FIG. 6b. Of the selected 19 clones, 9 clones possessed the 2G-C junction, and the other 10 clones the 3G-C junction. Comparing the arrangement of the 3 base pairs on the 3G-C junctions, 9 of the 10 clones had the same arrangement. 6 of the 9 clones with the 2G-C junction had a similar arrangement, and the remaining 3 clones had varied arrangement.

To further evaluate the structural requirement of the 3 base pairs on the junctions for the observed interaction, base pair substitutions on the junction of ch16-40 and ch9-48, which are deletion mutants including the intact three-way-junction region of clone 9 and 16 that demonstrate the lowest $K_d$ values, were carried out. The relative binding affinity for cholic acid of ch16-40 and ch9-48, which contains single-nucleotide substitution, is shown in Table 5. The number in the table indicates the relative affinity (%) taking the binding affinity of clones without substitution as 100.

TABLE 5

(a) ch9-48

| Original base pair | Relative binding affinity (%) | | | | | |
|---|---|---|---|---|---|---|
| | G5-C44 | 100 | G6-C31 | 100 | A32-T43 | 100 |
| Substituted base pair | C5-G44 | 74 | C6-G31 | 90 | T32-A43 | 93 |
| | A5-T44 | 46 | A6-T31 | 27 | G32-C43 | 57 |
| | I5-C44 | 44 | I6-C31 | 95 | I32-C43 | 5 |
| | G5-T44 | 0 | G6-T31 | 0 | G32-T43 | 0 |
| | C5-C44 | 0 | C6-C31 | 0 | T32-T43 | 0 |

(b) ch16-40

| Original base pair | Relative binding affinity (%) | | | | | |
|---|---|---|---|---|---|---|
| | G18-C5 | 100 | G19-C36 | 100 | G4-C37 | 100 |
| Substituted base pair | C18-G5 | 81 | C19-G36 | 86 | C4-G37 | 68 |
| | A18-T5 | 55 | A19-T36 | 63 | A4-T37 | 60 |
| | I18-C5 | 59 | I19-C36 | 42 | I4-C37 | 18 |
| | G18-T5 | 0 | G19-T36 | 0 | G4-T37 | 0 |
| | C18-C5 | 0 | G19-G36 | 0 | C4-C37 | 0 |

Interestingly, any substitutions by Watson-Crick base pairs did not lead to the loss of affinity whereas mismatched and wobble base pairs (G-T) completely resulted in the loss of affinity. By constructing a CPK model of the 6 nucleotides forming 3 Watson-Crick base pairs, these nucleotides were demonstrated to form a cyclophane-like cyclic structure consisting of 3 purine and 3 pyrimidine bases with a cavity of a inner diameter from 12 to 17 Å. Furthermore, the shape and size of this cavity is suited for the inclusion of cholic acid whose size is roughly 15 Å. Herein, a CPK model (Corey-Pauling-Koltun space filling molecular model) is a kind of molecular model of the spatial three-dimensional models. An improved molecular dynamics of the Corey-Pauling molecular model is merchandised by ad hoc committee to design and develop new atom and bond models of the US National Institutes of Health (NIH).

Even though with a few exceptions, the substitution with Watson-Crick base pairs did not influence the binding affinity. Substitutions from G-C to A-T reduced the binding affinity ($C_5$-$G_{36}$ to $T_5$-$A_{36}$: 56.1%; $C_6$-$G_{21}$ to $T_6$-$A_{21}$: 34.7%), whereas almost no reduction of the binding affinity was observed with substitution of A-T to G-C ($T_{22}$-$A_{35}$ to $C_{22}$-$G_{35}$: 95.2%). These results agree with the feature of the selected 19 clones having 2 or 3G-C within the junction and without junctions with 1 or none of the G-C base pairs.

EXAMPLE 4

Affinity of the DNA Aptamer Consisting of Two Molecules of the Present Invention The alterations in the ligand affinity due to mutations in the nucleotide sequence constituting the three-way junction in the aptamer of the present invention, which is constituted by two molecules, i.e. a target nucleotide sequence and a probe, were examined. More specifically, the affinity for cholic acid of the three-way junctions, wherein a target nucleotide sequence and a probe with nucleotide sequences described below were hybridized, was measured by SPR. 5 µM target nucleotide sequence and 5 µM probe were mixed, and the mixture was denatured with heat under the same condition as described in Example 1-(1). By loading 20 µl solution of the probe-target nucleotide sequence on a cholic acid-immobilized sensor chip BIAcore2000 (BlAcore), an SPR signal change of 600 RU (RU=resonance unit) was observed. On the other hand, when a single-nucleotide mutation had been introduced into the target nucleotide sequence (the underlined segment in the target nucleotide sequence was altered to CCTAGCAGCCGGAGCGGTGG (SEQ ID NO: 31). However, no SPR signal change could be observed. Additionally, not only the above sequence combination, but also when a mismatch had been introduced in the base pairs adjacent to the junction, the binding affinity decreased below the detectable level.

The sequence of the target nucleotide sequence/SEQ ID NO: 27 (the segment indicated with lower-case letters is complementary to the probe, and the junction is located at the position corresponding to the nucleotides flanking the single space)
5'-GTACCAGCTTATTCAATTACAGATC-
GAGGGCAGCGATAGCcctagcagcg ggagcggtg-gCATCGGTCCTGGACTTGGGACTAGAT-
AGTATGTTCATCAG-3'; and the sequence of the probe (CH3J-1-100)/SEQ ID NO: 28 (the segment indicated with lower-case letters is complementary to the target nucleotide sequence)
5'-ccaccgctccACTCAACTGGTTTTC-
CAGTTGAGTcgctgctagg-3'.

Next, using cholic acid, probe, and target nucleotide sequence (50 µM each), the amount of cholic acid binding to the probe-target nucleotide sequence complex was determined by the equilibrium-filtration method described in Example 2(1). The nucleotide sequences of the used target nucleotide sequence and probe are shown below:
the sequence of the target nucleotide sequence/SEQ ID NO: 29
5'-CCTAGCAGCGGGAGCGGTGG-3'; and
the sequence of the probe/SEQ ID NO: 30 (the segment indicated with lower-case letters is complementary to the target nucleotide sequence)
5'-ccaccgctccACTCAACTGGTTTTC-
CAGTTGAGTcgctgctagg-3'.

Result of the measurement demonstrated that the amount of bound cholic acid to be 36.6 µM (for ch2-40 under the same condition, the amount of bound cholic acid was 27.8 µM). On the other hand, when a single-nucleotide mutation had been introduced into the target nucleotide sequence (5'-CCTAGCAGCcGGAGCGGTGG-3'/SEQ ID NO: 31; the lower-case letter corresponds to the mutation), the sequence didn't bind cholic acid under the same condition (the amount of bound cholic acid was 0 µM).

EXAMPLE 5

Chemical Modification-Based Evaluation of the Secondary Structure of the Aptamer (1) Chemical Modification of Thymine with Osmium Tetraoxide The present inventors carried out chemical-modification studies on ch9-48 using an oxidizing agent, osmium tetroxide, to further evaluate the secondary structure of the aptamer and the bases related to the interaction. Osmium tetroxide selectively reacts with thymine (T) in a single-stranded state in the presence of pyridine (Furlong J. C. et al., Biochemistry, 28, 2009-2017, 1989). This selectivity is suggested to be the result of the activity of osmium tetroxide to attack C-5, 6 double bond of thymine (Nielsen P. E. et al., J.Mol.Recog., 3, 1-25, 1990). The sites of osmylation can be cleaved by alkaline treatment.

5 µM of 3'-FITC labeled ch9-48 or ch9-48-C6 were incubated with 100 µl binding buffer comprising 1 mM osmium tetroxide and 3% pyridine, with or without 5 mM cholic acid, for 15 min at 20° C. The control was incubated at 80° C. to denature the sequence to single strands. The reactions were stopped by two sequential ethanol precipitations. The aptamers were cleaved at the sites of osmate adducts (at the site of single stranded T) by the treatment with 15 µM of 1 M piperidine at 90° C. for 30 min. After the addition of 15 µl formamide loading buffer, the cleaved products were electrophoresed on 10% polyacrylamide gels (19%; the ratio of monomer:bis was 19:1) containing 7 M urea. The buffer system consisted of 90 mM Tris-borate (pH 8.0) and 2 mM EDTA. The gels were scanned and analyzed using FluorImager 595. The results are shown in FIG. 7.

(2) Experimental Results

Figure 7:
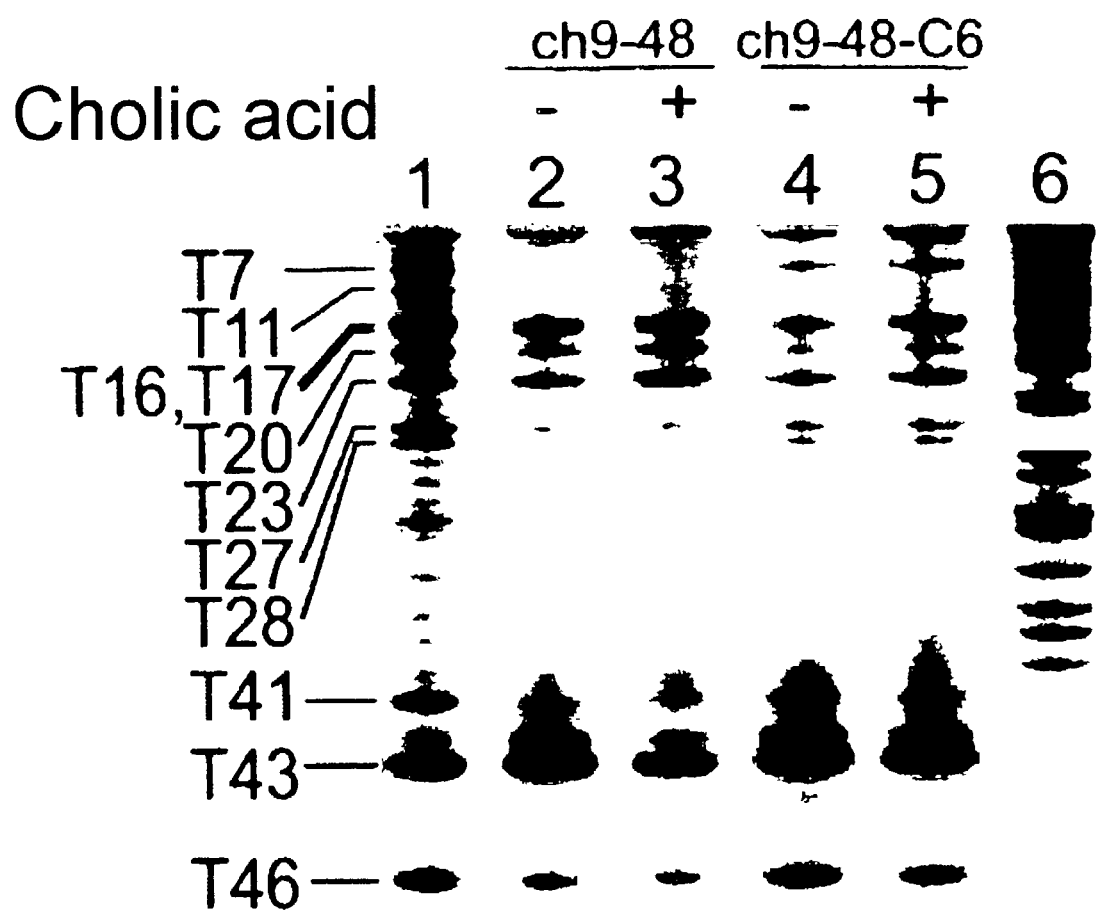
FIG. 7 depicts a photograph demonstrating the modification of thymine residues of ch9-48 and ch9-48-C6 with osmium tetraoxide.

The photograph demonstrating the result of polyacrylamide gel electrophoresis is depicted in FIG. 7. The pattern of modifications on ch9-48 under the folding condition (i.e., in the binding buffer at 20° C.) was highly consistent with the proposed secondary structure (FIG. 8). A strong modification was observed at T43 flanking the junction, while the T's in the loop regions were also highly reactive. The T's in the stem regions were efficiently protected except T23 and T46: T23 was reactive due to its position at the end of the stem region, and T46 seems to be reactive due to the instability of the short stem structure lacking a loop. A mutant ch9-48-C6, a mutant of ch9-48, which lacks the ability to bind to cholic acid, was prepared by substituting the 6th G to C, and the modification pattern was compared with ch9-48. In the presence of cholic acid, the degree of modification of T43 of ch9-48 at the branching point was reduced to less than 40%. In contrast, the reactivity of T43 in ch9-48-C6 was only slightly suppressed by cholic acid. Thus, T43 in ch9-48 appears to be directly involved in the binding with cholic acid.

INDUSTRIAL APPLICABILITY

The present invention provides a novel detection method for target nucleotide sequences utilizing a nucleic acid aptamer formation. A specific detection of SNP is possible by the detection method of the present invention due to the use of a nucleic acid aptamer whose ligand-binding affinity greatly changes depending on the presence of a single-nucleotide mismatch. No detection principle wherein a single-nucleotide mismatch provides such significant difference has been known in the art.

Furthermore, the present invention provides nucleic acid aptamers with a novel structure that is useful for detecting target nucleotide sequences of the present invention. The ligand-binding affinity of the nucleic acid aptamers of the present invention that capture a ligand, such as cholic acid, at the three-way junction is lost by a mismatch alone in any one of the three base pairs of the three junction moiety. Thus, the nucleic acid aptamers comprising the three-way junction are highly preferable for the application to the detection method of SNPs.

SEQUENCE LISTING

<160> NUMBER OF SEQ ID NOS: 31

<210> SEQ ID NO 1
<211> LENGTH: 100
<212> TYPE: DNA
<213> ORGANISM: Artificial Sequence
<220> FEATURE:
<223> OTHER INFORMATION: Description of Artificial Sequence:
      Artificially Synthesized Sequence
<220> FEATURE:
<221> NAME/KEY: misc_feature
<222> LOCATION: 19-82
<223> OTHER INFORMATION: n = any nucleotide

<400> SEQUENCE: 1
gtaccagctt attcaattnn nnnnnnnnnn nnnnnnnnnn nnnnnnnnnn nnnnnnnnnn    60
nnnnnnnnnn nnnnnnnnnn nnagatagta tgttcatcag                         100

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 2
ctgatgaaca tactatct                                                  18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 3
gtaccagctt attcaatt                                                  18

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 4
gagggcagcg atagctgggc taataaggtt agccccatc                           39

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 5
gcgccgattg acccaaatcg ttttgtatgc aaaagcgc                            38

<210> SEQ ID NO 6
<211> LENGTH: 47
<212> TYPE: DNA

```
<213> ORGANISM: Artificial Sequence
<220> FEATURE:
<223> OTHER INFORMATION: Description of Artificial Sequence:
      Artificially Synthesized Sequence

<400> SEQUENCE: 6
gatcgagggc agcgatagct gggctaataa ggttagcccc atcggtc              47

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 7
agcgccgatt gacccaaatc gttttgtatg caaaagcgct                      40

<210> SEQ ID NO 8
<211> LENGTH: 100
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 8
gtaccagctt attcaattac agatcgaggg cagcgatagc tgggctaata aggttagccc    60
catcggtcct ggacttggga ctagatagta tgttcatcag                         100

<210> SEQ ID NO 9
<211> LENGTH: 100
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 9
gtaccagctt attcaattag cgccgattga cccaaatcgt ttgtatgca aaagcgctgc     60 tggtatcaac tgttacccat gaagatagta tgttcatcag                         100

<210> SEQ ID NO 10
<211> LENGTH: 100
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 10
gtaccagctt attcaattcg cggaagacga attccaagcg cgcgcgggtc acgcgacttg    60
ggaatgagca agggttggcc cgagatagta tgttcatcag                         100

<210> SEQ ID NO 11
<211> LENGTH: 100
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 11
gtaccagctt attcaattgg gcgaaggaac atacggcagt ttatggccgc tatcgagata    60
```
gactatcatc tcaacgtctt ctagatagta tgttcatcag        100

<210> SEQ ID NO 12
<211> LENGTH: 100
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 12
gtaccagctt attcaattgc gagcagggtc aatggaatta atgatcaatt gacagacgca        60
agtctcctgc ggtcctgtgt tgagatagta tgttcatcag        100

<210> SEQ ID NO 13
<211> LENGTH: 99
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 13
gtaccagctt attcaattac acggacagag ggtagcggct ctgcgcattg agttgctgcg        60
ggctgaagcc cggtacatgg gagatagtat gttcatcag        99

<210> SEQ ID NO 14
<211> LENGTH: 100
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 14
gtaccagctt attcaattag ggatcggacg tgagggcgat aggcgaaacg tcaagggtga        60
gagtaaggag ggcttcgatt ccagatagta tgttcatcag        100

<210> SEQ ID NO 15
<211> LENGTH: 99
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 15
gtaccagctt attcaattgg acgtaggcga agttggcgga gttaggattt tgaagaaggc        60
taaacacctt agcctgggac tagatagtat gttcatcag        99

<210> SEQ ID NO 16
<211> LENGTH: 100
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 16
gtaccagctt attcaattac cgcgaagaag tgtcattgtt ttggagattc gaagcgctgt        60
acacaggtaa tgaagccttc taagatagta tgttcatcag        100

```
<210> SEQ ID NO 17
<211> LENGTH: 100
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 17
gtaccagctt attcaattac aacggaggcc aagggactcc cacgctttt atagcgggc      60 gatgtttgag aagtctccca cgagatagta tgttcatcag                         100

<210> SEQ ID NO 18
<211> LENGTH: 100
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 18
gtaccagctt attcaattcg acaacgaggg gcggagtatc cgaaattggc ggcgtaaagc   60
aattgtagtt aagctctcat gtagatagta tgttcatcag                         100

<210> SEQ ID NO 19
<211> LENGTH: 100
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 19
gtaccagctt attcaattgc caccgcgagg tgcgaaacgg gtacgaaaca attcagcccg   60
tctcggcatt tgacttgcgt ttagatagta tgttcatcag                         100

<210> SEQ ID NO 20
<211> LENGTH: 100
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 20
gtaccagctt attcaattgg gaacgatgaa ttattcgggc cctgagttgt tagaactcag   60
caattgttgg tgtcacctat taagatagta tgttcatcag                         100

<210> SEQ ID NO 21
<211> LENGTH: 100
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 21
gtaccagctt attcaattag tcaactggag gttggtcgca agacactaat ttcagtctct   60
tacgattgcc gccgggagtg tgagatagta tgttcatcag                         100

<210> SEQ ID NO 22
<211> LENGTH: 100
<212> TYPE: DNA
<213> ORGANISM: Artificial Sequence
```

```
<220> FEATURE:
<223> OTHER INFORMATION: Description of Artificial Sequence:
      Artificially Synthesized Sequence

<400> SEQUENCE: 22
gtaccagctt attcaattgc ccgggatgtg aacggaacg gcgataactt agttttatcg      60
gcagttggat ggaatgtgcc ttagatagta tgttcatcag                          100

<210> SEQ ID NO 23
<211> LENGTH: 95
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 23
gtaccagctt attcaattgg cagcggacta caggccggat gacgttagcg acatcctgct     60
tataagctta tggtcgtaga tagtatgttc atcag                                95

<210> SEQ ID NO 24
<211> LENGTH: 99
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 24
gtaccagctt attcaattgg ggttgtaaca aggcaattag acgacaattg ggcagcattc     60
tgccaataag tatggttatt gagatagtat gttcatcag                            99

<210> SEQ ID NO 25
<211> LENGTH: 97
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 25
gtaccagctt attcaattcg acgcagaaga taaataacag cagacttcct gctggctggc     60
tttccgctca tcttcgccaa gatagtatgt tcatcag                              97

<210> SEQ ID NO 26
<211> LENGTH: 100
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 26
gtaccagctt attcaattac gtcgaaaggt ttcggcgaga gggcatcaag tgccgctcat     60
agagcctcga gtccataccc tgagatagta tgttcatcag                          100

<210> SEQ ID NO 27
<211> LENGTH: 100
<212> TYPE: DNA
<213> ORGANISM: Artificial Sequence
<220> FEATURE:
<223> OTHER INFORMATION: Description of Artificial Sequence:
      Artificially Synthesized Sequence
```

-continued

```
<400> SEQUENCE: 27
gtaccagctt attcaattac agatcgaggg cagcgatagc cctagcagcg ggagcggtgg        60
catcggtcct ggacttggga ctagatagta tgttcatcag                             100

<210> SEQ ID NO 28
<211> LENGTH: 44
<212> TYPE: DNA
<213> ORGANISM: Artificial Sequence
<220> FEATURE:
<223> OTHER INFORMATION: Description of Artificial Sequence:
      Artificially Synthesized Probe Sequence

<400> SEQUENCE: 28
ccaccgctcc actcaactgg ttttccagtt gagtcgctgc tagg                        44

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 29
cctagcagcg ggagcggtgg                                                   20

<210> SEQ ID NO 30
<211> LENGTH: 44
<212> TYPE: DNA
<213> ORGANISM: Artificial Sequence
<220> FEATURE:
<223> OTHER INFORMATION: Description of Artificial Sequence:
      Artificially Synthesized Probe Sequence

<400> SEQUENCE: 30
ccaccgctcc actcaactgg ttttccagtt gagtcgctgc tagg                        44

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 31
cctagcagcc ggagcggtgg                                                   20
```

The invention claimed is:

1. A method for detecting a target nucleotide sequence, which comprises the steps of:
   (a) hybridizing a probe to the target nucleotide sequence to form a nucleic acid aptamer having a ligand-binding affinity, wherein the ligand is cholic acid, and wherein the aptamer has three stems and binds with the ligand at the position where the three stems intersect; and
   (b) detecting the presence of the target nucleotide sequence using the ligand-binding affinity of the aptamer as an index.

2. The method of claim 1, wherein the target nucleotide sequence contains a single nucleotide polymorphism, and the affinity of the formed aptamer for the cholic acid ligand varies depending on the substitution of the single nucleotide in the target molecule.

3. The method of claim 1, wherein at least two of three base pairs at the position where the three stems intersect are G-C nucleotide pairs.

4. The method of claim 3, wherein each of the three stems is longer than three base pairs.

* * * * *

UNITED STATES PATENT AND TRADEMARK OFFICE
CERTIFICATE OF CORRECTION

PATENT NO.         : 7,303,867 B2
APPLICATION NO. : 10/149869
DATED               : December 4, 2007
INVENTOR(S)      : Karube et al.

Page 1 of 1

It is certified that error appears in the above-identified patent and that said Letters Patent is hereby corrected as shown below:

On the cover page,

[*] Notice:    Subject to any disclaimer, the term of this patent is extended or adjusted under 35 USC 154(b) by 359 days Delete the phrase "by 359 days" and insert -- by 423 days --

Signed and Sealed this

Seventh Day of April, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,303,867 B2  Page 1 of 13
APPLICATION NO. : 10/149869
DATED : December 4, 2007
INVENTOR(S) : Isao Karube et al.

It is certified that error appears in the above-identified patent and that said Letters Patent is hereby corrected as shown below:

Col. 23,
Please replace the incorrect Sequence Listing contained in the above-identified issued patent with the correct Sequence Listing that was filed in the above-identified application, as set forth below.

```
<110> KARUBE, ISAO
      KATO, TERU

<120> METHOD FOR DETECTING TARGET NUCLEOTIDE SEQUENCES

<130> SHZ-003US

<140> 10/149,869
<141> 2002-12-23

<150> PCT/JP00/08909
<151> 2000-12-15

<150> JP 1999-357913
<151> 1999-12-16

<160> 48

<170> PatentIn Ver. 3.3

<210> 1
<211> 100
<212> DNA
<213> Artificial Sequence

<220>
<223> Description of Artificial Sequence: Synthetic
      oligonucleotide

<220>
<221> modified_base
<222> (19)..(82)
<223> a, c, g, t, unknown or other
```

Signed and Sealed this

Seventh Day of September, 2010

David J. Kappos
*Director of the United States Patent and Trademark Office*

<400> 1
gtaccagctt attcaattnn nnnnnnnnnn nnnnnnnnnn nnnnnnnnnn nnnnnnnnnn 60
nnnnnnnnnn nnnnnnnnnn nnagatagta tgttcatcag                       100

<210> 2
<211> 18
<212> DNA
<213> Artificial Sequence

<220>
<223> Description of Artificial Sequence: Synthetic
      primer

<400> 2
ctgatgaaca tactatct                                               18

<210> 3
<211> 18
<212> DNA
<213> Artificial Sequence

<220>
<223> Description of Artificial Sequence: Synthetic
      primer

<400> 3
gtaccagctt attcaatt                                               18

<210> 4
<211> 39
<212> DNA
<213> Artificial Sequence

<220>
<223> Description of Artificial Sequence: Synthetic
      oligonucleotide

<400> 4
gagggcagcg atagctgggc taataaggtt agccccatc                        39

<210> 5
<211> 38
<212> DNA
<213> Artificial Sequence

<220>
<223> Description of Artificial Sequence: Synthetic
      oligonucleotide

<400> 5
gcgccgattg acccaaatcg ttttgtatgc aaaagcgc                         38

<210> 6
<211> 47
<212> DNA
<213> Artificial Sequence

<220>
<223> Description of Artificial Sequence: Synthetic
     oligonucleotide

<400> 6
gatcgagggc agcgatagct gggctaataa ggttagcccc atcggtc            47

<210> 7
<211> 40
<212> DNA
<213> Artificial Sequence

<220>
<223> Description of Artificial Sequence: Synthetic
     oligonucleotide

<400> 7
agcgccgatt gacccaaatc gttttgtatg caaaagcgct                    40

<210> 8
<211> 100
<212> DNA
<213> Artificial Sequence

<220>
<223> Description of Artificial Sequence: Synthetic
     oligonucleotide

<400> 8
gtaccagctt attcaattac agatcgaggg cagcgatagc tgggctaata aggttagccc    60
catcggtcct ggacttggga ctagatagta tgttcatcag                         100

<210> 9
<211> 100
<212> DNA
<213> Artificial Sequence

<220>
<223> Description of Artificial Sequence: Synthetic
     oligonucleotide

<400> 9
gtaccagctt attcaattag cgccgattga cccaaatcgt tttgtatgca aaagcgctgc    60
tggtatcaac tgttacccat gaagatagta tgttcatcag                         100

<210> 10
<211> 100
<212> DNA

<213> Artificial Sequence

<220>
<223> Description of Artificial Sequence: Synthetic
      oligonucleotide

<400> 10
gtaccagctt attcaattcg cggaagacga attccaagcg cgcgcgggtc acgcgacttg   60
ggaatgagca agggttggcc cgagatagta tgttcatcag                          100

<210> 11
<211> 100
<212> DNA
<213> Artificial Sequence

<220>
<223> Description of Artificial Sequence: Synthetic
      oligonucleotide

<400> 11
gtaccagctt attcaattgg gcgaaggaac atacggcagt ttatggccgc tatcgagata   60
gactatcatc tcaacgtctt ctagatagta tgttcatcag                          100

<210> 12
<211> 100
<212> DNA
<213> Artificial Sequence

<220>
<223> Description of Artificial Sequence: Synthetic
      oligonucleotide

<400> 12
gtaccagctt attcaattgc gagcagggtc aatggaatta atgatcaatt gacagacgca   60
agtctcctgc ggtcctgtgt tgagatagta tgttcatcag                          100

<210> 13
<211> 99
<212> DNA
<213> Artificial Sequence

<220>
<223> Description of Artificial Sequence: Synthetic
      oligonucleotide

<400> 13
gtaccagctt attcaattac acggacagag ggtagcggct ctgcgcattg agttgctgcg   60
ggctgaagcc cggtacatgg gagatagtat gttcatcag                           99

<210> 14
<211> 100
<212> DNA
<213> Artificial Sequence

<220>
<223> Description of Artificial Sequence: Synthetic
      oligonucleotide

<400> 14
gtaccagctt attcaattag ggatcggacg tgagggcgat aggcgaaacg tcaagggtga  60
gagtaaggag ggcttcgatt ccagatagta tgttcatcag                        100

<210> 15
<211> 99
<212> DNA
<213> Artificial Sequence

<220>
<223> Description of Artificial Sequence: Synthetic
      oligonucleotide

<400> 15
gtaccagctt attcaattgg acgtaggcga agttggcgga gttaggattt tgaagaaggc  60
taaacacctt agcctgggac tagatagtat gttcatcag                         99

<210> 16
<211> 100
<212> DNA
<213> Artificial Sequence

<220>
<223> Description of Artificial Sequence: Synthetic
      oligonucleotide

<400> 16
gtaccagctt attcaattac cgcgaagaag tgtcattgtt ttggagattc gaagcgctgt  60
acacaggtaa tgaagccttc taagatagta tgttcatcag                        100

<210> 17
<211> 100
<212> DNA
<213> Artificial Sequence

<220>
<223> Description of Artificial Sequence: Synthetic
      oligonucleotide

<400> 17
gtaccagctt attcaattac aacggaggcc aagggactcc cacgcttttt atagcggggc  60
gatgtttgag aagtctccca cgagatagta tgttcatcag                        100

<210> 18
<211> 100
<212> DNA
<213> Artificial Sequence

<220>
<223> Description of Artificial Sequence: Synthetic
      oligonucleotide

<400> 18
gtaccagctt attcaattcg acaacgaggg gcggagtatc cgaaattggc ggcgtaaagc  60
aattgtagtt aagctctcat gtagatagta tgttcatcag                       100

<210> 19
<211> 100
<212> DNA
<213> Artificial Sequence

<220>
<223> Description of Artificial Sequence: Synthetic
      oligonucleotide

<400> 19
gtaccagctt attcaattgc cacggcgagg tgcgaaacgg gtacgaaaca attcagcccg  60
tctcggcatt tgacttgcgt ttagatagta tgttcatcag                       100

<210> 20
<211> 100
<212> DNA
<213> Artificial Sequence

<220>
<223> Description of Artificial Sequence: Synthetic
      oligonucleotide

<400> 20
gtaccagctt attcaattgg gaacgatgaa ttattcgggc cctgagttgt tagaactcag  60
caattgttgg tgtcacctat taagatagta tgttcatcag                       100

<210> 21
<211> 100
<212> DNA
<213> Artificial Sequence

<220>
<223> Description of Artificial Sequence: Synthetic
      oligonucleotide

<400> 21
gtaccagctt attcaattag tcaactggag gttggtcgca agacactaat ttcagtctct  60
tacgattgcc gcgggagtg tgagatagta tgttcatcag                        100

<210> 22
<211> 100
<212> DNA
<213> Artificial Sequence

<220>

<223> Description of Artificial Sequence: Synthetic
     oligonucleotide

<400> 22
gtaccagctt attcaattgc ccgggatgtg gaacggaacg gcgataactt agttttatcg 60
gcagttggat ggaatgtgcc ttagatagta tgttcatcag                       100

<210> 23
<211> 95
<212> DNA
<213> Artificial Sequence

<220>
<223> Description of Artificial Sequence: Synthetic
     oligonucleotide

<400> 23
gtaccagctt attcaattgg cagcggacta caggccggat gacgttagcg acatcctgct 60
tataagctta tggtcgtaga tagtatgttc atcag                            95

<210> 24
<211> 99
<212> DNA
<213> Artificial Sequence

<220>
<223> Description of Artificial Sequence: Synthetic
     oligonucleotide

<400> 24
gtaccagctt attcaattgg ggttgtaaca aggcaattag acgacaattg ggcagcattc 60
tgccaataag tatggttatt gagatagtat gttcatcag                        99

<210> 25
<211> 97
<212> DNA
<213> Artificial Sequence

<220>
<223> Description of Artificial Sequence: Synthetic
     oligonucleotide

<400> 25
gtaccagctt attcaattcg acgcagaaga taaataacag cagacttcct gctggctggc 60
tttccgctca tcttcgccaa gatagtatgt tcatcag                          97

<210> 26
<211> 100
<212> DNA
<213> Artificial Sequence

<220>
<223> Description of Artificial Sequence: Synthetic oligonucleotide

<400> 26
gtaccagctt attcaattac gtcgaaaggt ttcggcgaga gggcatcaag tgccgctcat    60
agagcctcga gtccataccc tgagatagta tgttcatcag                          100

<210> 27
<211> 100
<212> DNA
<213> Artificial Sequence

<220>
<223> Description of Artificial Sequence: Synthetic
      oligonucleotide

<400> 27
gtaccagctt attcaattac agatcgaggg cagcgatagc cctagcagcg ggagcggtgg    60
catcggtcct ggacttggga ctagatagta tgttcatcag                          100

<210> 28
<211> 44
<212> DNA
<213> Artificial Sequence

<220>
<223> Description of Artificial Sequence: Synthetic
      oligonucleotide

<400> 28
ccaccgctcc actcaactgg ttttccagtt gagtcgctgc tagg                     44

<210> 29
<211> 20
<212> DNA
<213> Artificial Sequence

<220>
<223> Description of Artificial Sequence: Synthetic
      oligonucleotide

<400> 29
cctagcagcg ggagcggtgg                                                20

<210> 30
<211> 44
<212> DNA
<213> Artificial Sequence

<220>
<223> Description of Artificial Sequence: Synthetic
      oligonucleotide

<400> 30
ccaccgctcc actcaactgg ttttccagtt gagtcgctgc tagg     44

<210> 31
<211> 20
<212> DNA
<213> Artificial Sequence

<220>
<223> Description of Artificial Sequence: Synthetic
       oligonucleotide <400> 31
cctagcagcc ggagcggtgg     20

<210> 32
<211> 63
<212> DNA
<213> Artificial Sequence

<220>
<223> Description of Artificial Sequence: Synthetic
       oligonucleotide <400> 32
gggatcggac gtgagggcga taggcgaaac gtcaagggtg agagtaagga gggcttcgat     60
tcc     63

<210> 33
<211> 74
<212> DNA
<213> Artificial Sequence

<220>
<223> Description of Artificial Sequence: Synthetic
       oligonucleotide <400> 33
ccagcttatt caattggacg taggcgaagt tggcggagtt aggattttga agaaggctaa     60
acaccttagc ctgg     74

<210> 34
<211> 63
<212> DNA
<213> Artificial Sequence

<220>
<223> Description of Artificial Sequence: Synthetic
       oligonucleotide <400> 34
gcttattcaa ttcgcggaag acgaattcca agcgcgcgcg ggtcacgcga cttgggaatg     60
agc     63

<210> 35
<211> 56
<212> DNA
<213> Artificial Sequence

<220>
<223> Description of Artificial Sequence: Synthetic
      oligonucleotide

<400> 35
attaccgcga agaagtgtca ttgtttttgga gattcgaagc gctgtacaca ggtaat      56

<210> 36
<211> 69
<212> DNA
<213> Artificial Sequence

<220>
<223> Description of Artificial Sequence: Synthetic
      oligonucleotide

<400> 36
gaacatacgg cagtttatgg ccgctatcga gatagactat catctcaacg tcttctagat  60
agtatgttc                                                          69

<210> 37
<211> 47
<212> DNA
<213> Artificial Sequence

<220>
<223> Description of Artificial Sequence: Synthetic
      oligonucleotide

<400> 37
acaacggagg ccaagggact cccacgcttt ttatagcggg gcgatgt                 47

<210> 38
<211> 48
<212> DNA
<213> Artificial Sequence

<220>
<223> Description of Artificial Sequence: Synthetic
      oligonucleotide

<400> 38
gcagggtcaa tggaattaat gatcaattga cagacgcaag tctcctgc                48

<210> 39
<211> 52

<212> DNA
<213> Artificial Sequence

<220>
<223> Description of Artificial Sequence: Synthetic
      oligonucleotide

<400> 39
caattcgaca acgaggggcg gagtatccga aattggcggc gtaaagcaat tg         52

<210> 40
<211> 76
<212> DNA
<213> Artificial Sequence

<220>
<223> Description of Artificial Sequence: Synthetic
      oligonucleotide

<400> 40
gtaccagctt attcaattac acggacagag ggtagcggct ctgcgcattg agttgctgcg   60
ggctgaagcc cggtac                                                  76

<210> 41
<211> 61
<212> DNA
<213> Artificial Sequence

<220>
<223> Description of Artificial Sequence: Synthetic
      oligonucleotide

<400> 41
tcaattgcca ccgcgaggtg cgaaacgggt acgaaacaat tcagcccgtc tcggcatttg   60
a                                                                  61

<210> 42
<211> 53
<212> DNA
<213> Artificial Sequence

<220>
<223> Description of Artificial Sequence: Synthetic
      oligonucleotide

<400> 42
caattgggaa cgatgaatta ttcgggccct gagttgttag aactcagcaa ttg         53

<210> 43
<211> 37
<212> DNA
<213> Artificial Sequence

<220>
<223> Description of Artificial Sequence: Synthetic
      oligonucleotide

<400> 43
aattagtcaa ctggaggttg gtcgcaagac actaatt                              37

<210> 44
<211> 54
<212> DNA
<213> Artificial Sequence

<220>
<223> Description of Artificial Sequence: Synthetic
      oligonucleotide

<400> 44
caattgcccg ggatgtggaa cggaacggcg ataacttagt tttatcggca gttg           54

<210> 45
<211> 40
<212> DNA
<213> Artificial Sequence

<220>
<223> Description of Artificial Sequence: Synthetic
      oligonucleotide

<400> 45
gcagcggact acaggccgga tgacgttagc gacatcctgc                           40

<210> 46
<211> 63
<212> DNA
<213> Artificial Sequence

<220>
<223> Description of Artificial Sequence: Synthetic
      oligonucleotide

<400> 46
cttattcaat tggggttgta acaaggcaat tagacgacaa ttgggcagca ttctgccaat     60
aag                                                                   63

<210> 47
<211> 56
<212> DNA
<213> Artificial Sequence

<220>
<223> Description of Artificial Sequence: Synthetic
      oligonucleotide

<400> 47
ccagcttatt caattcgacg cagaagataa ataacagcag acttcctgct ggctgg    56

<210> 48
<211> 40
<212> DNA
<213> Artificial Sequence

<220>
<223> Description of Artificial Sequence: Synthetic
      oligonucleotide

<400> 48
ggcgagaggg catcaagtgc cgctcataga gcctcgagtc    40